(12) United States Patent
Tomatsu et al.

(10) Patent No.: US 7,943,126 B2
(45) Date of Patent: May 17, 2011

(54) COMPOSITIONS AND METHODS FOR TREATING HYPOPHOSPHATASIA

(75) Inventors: Shunji Tomatsu, Saint Louis, MO (US);
William S Sly, Saint Louis, MO (US);
Jeffrey H Grubb, Saint Louis, MO (US); Tatsuo Nishioka, Kanazawa (JP);
Ken-ichi Miyamoto, Kanazawa (JP);
Seiji Yamaguchi, Izumo (JP)

(73) Assignee: Saint Louis University, Saint Louis, MO (US)

( * ) Notice: Subject to any disclaimer, the term of this patent is extended or adjusted under 35 U.S.C. 154(b) by 0 days.

(21) Appl. No.: 12/405,920

(22) Filed: Mar. 17, 2009

(65) Prior Publication Data

US 2009/0238814 A1 Sep. 24, 2009

Related U.S. Application Data

(62) Division of application No. 11/484,870, filed on Jul. 11, 2006, now abandoned.

(51) Int. Cl.
*A61K 38/43* (2006.01)
*A61P 19/08* (2006.01)
*C12N 9/00* (2006.01)
*C12P 21/02* (2006.01)

(52) U.S. Cl. ........ 424/94.1; 514/12; 530/350; 435/69.1; 435/183

(58) Field of Classification Search ................ 424/94.1; 435/69.1, 183; 514/12; 530/350
See application file for complete search history.

(56) References Cited

U.S. PATENT DOCUMENTS

| 6,455,495 | B1 | 9/2002 | Orgel et al. |
| 2005/0276796 | A1 | 12/2005 | Tomatsu et al. |
| 2006/0014687 | A1 | 1/2006 | Crine et al. |

OTHER PUBLICATIONS

Boskey et al., Matrix vesicles promote mineralization in a gelatin gel. Calcif. Tissue Int. 60 (1997) 309-315.
A.L. Boskey, Amorphous calcium phosphate: the contention of bone. J. Dent. Res. 76 (1997) 1433-1436.
J.L Meyer, Can biological calcification occur in the presence of pyrophosphate? Arch. Biochem. Biophys. 15 (1984) 1-8.
Moss et al., Association of inorganic-pyrophosphatase activity with human alkaline-phosphatase preparations. Biochem. J. 102 (1967) 53-57.
Leone et al., Allosteric modulation of pyrophosphatase activity of rat osseous plate alkaline phosphatase by magnesium ions. Int. J. Biochem. Cell Biol. 30 (1998) 89-97.
Russell et al., Inorganic pyrophosphate in plasma in normal persons and in patients with hypophosphatasia, osteogenesis imperfecta, and other disorders of bone. J. Clin. Invest. 50 (1971) 961-965.
Anderson et al., Matrix vesicles in osteomalacic hypophosphatasia bone contain apatite-like mineral crystals. Am. J. Pathol. 151 (1997) 1555-1561.
Anderson et al., Impaired calcification around matrix vesicles of growth plate and bone in alkaline phosphatase-deficient mice. Am. J. Pathol. 164 (2004)841-847.
Barton et al., Replacement therapy for inherited enzyme deficiency-macrophage-targeted glucocerebrosidase for Gaucher's disease. N. Engl. J. Med. 324 (1991) 1464-1470. (Abstract Only).
Sands et al., Enzyme replacement therapy for murine mucopolysaccharidosis type VII. J. Clin. Invest. 93 (1994) 2324-2331.
Shull et al., Enzyme replacement in a canine model of Hurler syndrome. Proc. Natl. Acad. Sci. 91 (1994) 12937-12941.
Crawley et al., Enzyme replacement therapy in a feline model of Maroteaux-Lamy syndrome. J. Clin. Invest. 97 (1996) 1864-1873.
Kakkis et al., Enzyme-replacement therapy in mucopolysaccharidosis I. N. Engl. J. Med. 344 (2001) 182-188.
Altarescu, et al., The efficacy of enzyme replacement therapy in patients with chronic neuronopathic Gaucher's disease. J. Pediatr. 138 (2001) 539-547.
Eng et al., International Collaborative Fabry Disease Study Group, Safety and efficacy of recombinant human alpha galactosidase A-replacement therapy in Fabry's disease. N. Eng!. J. Med. 345 (2001) 9-16.
Furbish et al., Uptake and distribution of placental glucocerebrosidase in rat hepatic cells and effects of sequential deglycosylation. Biochim. Biophys. Acta. 673 (1981) 425-434.
G.J. Murray, Lectin-specific targeting of lysosomal enzymes to reticuloendothelial cells. Methods Enzymol. 149 (1987) 25-42.
Stahl et al., Evidence for receptor-mediated binding of glycoproteins, glycoconjugates, and glycosidases by alveolar macrophages. Proc. Natl. Acad. Sci. 75 (1978) 1399-1403.
Achord et al., Human beta-glucuronidase: in vivo clearance and in vitro uptake by a glycoprotein recognition system on reticuloendothelial cells. Cell 15 (1978) 269-278.
Whyte et al., Infantile hypophosphatasia: enzyme replacement therapy by intravenous infusion of alkaline phosphatase-rich plasma from patients with Paget bone disease. J. Pediatr. 101 (1982) 379-386.
Whyte et al., Enzyme replacement therapy for infantile hypophosphatasia attempted by intravenous infusions of \ / alkaline phosphatase-rich Paget plasma: results in three additional patients. J. Pediatr. 105 (1984) 926-933.
Whyte et al., Infantile hypophosphatasia: normalization of circulating bone alkaline phosphatase activity followed by KKH 23 skeletal remineralization. Evidence for an intact structural gene for tissue nonspecific alkaline phosphatase. J. Pediatr. D 108 (1986) 82-88.
Weninger et al.. Biochemical and morphological effects of human hepatic alkaline phosphatase in a neonate with D hypophosphatasia. Acta Paediatr. Scand. SUppl. 360 (1989) 154-160.
Whyte et al., Alkaline phosphatase: placental and tissue-nonspecific isoenzymes hydrolyze phosphoethanolamine, 25 inorganic pyrophosphatem and pyridoxal5'-phosphate. Substrate accumulation in carriers of hypophosphatasia D corrects during pregnancy. J. Clin. Invest. 95 (1995) 1440-1445.

(Continued)

*Primary Examiner* — Kevin K. Hill
(74) *Attorney, Agent, or Firm* — Randolph Bretton; The Law Office of Randolph Bretton

(57) ABSTRACT

The present invention provides compositions and methods for use in enzyme replacement therapy. The inventors disclose a method of producing membrane bound enzymes in an active soluble form by eliminating the glycosylphosphatidylinositol (GPI) membrane anchor. In particular the inventors disclose a soluble active form of the membrane bound enzyme TNSALP which they produced by deleting the GPI anchor single peptide sequence. They have further shown that this composition is useful for treatment of hypophosphatasia. The inventors also disclose oligo acid amino acid variants thereof which specifically target bone tissue.

18 Claims, 12 Drawing Sheets

OTHER PUBLICATIONS

Narisawa et al., Abnormal vitamin B6 metabolism in alkaline phosphatase knock-out mice causes mUltiple abnormalities, but not the impaired bone mineralization. J Pathol. 191 (2001) 125-133.

Nishioka et al.. Enhancement of drug delivery to bone: Characterization of human tissue-nonspecific alkaline phosphatase tagged with an acidic oligopeptide. Mol Genet Metab. Jul. 2006; 88(3):244-255. Epub Apr. 17, 2006.

Kasugai, et al., Selective Drug Delivery System to Bone: Small Peptide (Asp)6 Conjugation, (2000) J. Bone. Miner. Res. 15, 936-943.

Yokogawa et al., Selective Delivery of Estradiol to Bone by Aspartic Acid Oligopeptide and Its Effects on Ovariectomized Mice, (2001) Endocrinology 142,1228-1233.

Waymire et al., Mice lacking tissue non-specific alkaline phosphatase die from seizures due to defective metabolism of vitamin B-6. Nat. Genet. 11 (1995) 45-51.

Narisawa et al., Inactivation of two mouse alkaline phosphatase genes and establishment of a model of infantile hypophosphatasia. Dev. Dyn. 208 (1997) 432-446.

M. Whyte, Hypophosphatasia and the Role of Alkaline Phosphatase in Skeletal Mineralization, Endocrine Reviews, (1994), vol. 15, No. 4, 439-461.

Weiss et al., Structure of the Human Liver/BonelKidney Alkaline Phasphatase Gene, The Journal of Biological Chemistry, (1988) Vo. 263, No. 24,12002-12010.

ODA et al, A General Method for Rapid Purification of Soluble Versions of Glycosyhosphatidylinositol-Anchored Proteins Expressed in Insect Cells: An Application for Human Tissue-Nonspecific Alkaline Phosphatase, J. Biochem 126: 694-699,(1999).

Kaufmann et al., Influence of low temperature on productivity, proteome and protein phosphorylation of CHO cells. Biotechnol. Bioeng. 63(5): 573-582, 1999; Abstract only.

Michigami et al., Common mutations F310L and T1559del in the tissue-nonspecific alkaline phosphatase gene are related to distinct phenotypes in Japanese patients with hypophosphatasia, Eur. J. Pediatr. 164: 277-282, 2005.

US 7,943,126 B2

COMPOSITIONS AND METHODS FOR TREATING HYPOPHOSPHATASIA

PARENT CASE TEXT

This application is a divisional application of U.S. patent application Ser. No. 11/484,870 filed Jul. 11, 2006 pending and claims benefit of priority to U.S. Provisional Patent Application No. 60/725,563, filed Oct. 11, 2005. All documents above are incorporated herein in their entirety by reference.

SEQUENCE LISTING

A paper copy of the sequence listing and a computer readable form of the same sequence listing are appended below and herein incorporated by reference. The information recorded in computer readable form is identical to the written sequence listing, according to 37 C.F.R. 1.821 (f).

BACKGROUND OF THE INVENTION

1. Field of the Invention

This invention relates generally to compositions and methods of enzyme replacement therapy (ERT). More specifically, the invention is directed to compositions and methods for treatment of enzyme deficient disease such as hypophosphatasia using a genetically modified polynucleotide to produce in an active secretory form of alkaline phosphatase.

2. Description of the Related Art

Alkaline phosphatase (ALP) is a ubiquitous plasma membrane-bound enzyme. Hypophosphatasia is an inherited metabolic disorder of defective bone mineralization caused by deficiency of a form of ALP know as tissue-nonspecific alkaline phosphatase (TNSALP). Clinical severity is remarkably variable, ranging from death in utero to merely premature loss of dentition in adult life [1, 2]. Despite the presence of TNSALP in bone, kidney, liver, and adrenal tissue in healthy individuals, clinical manifestations in patients with hypophosphatasia are limited to defective skeletal mineralization that manifests as rickets in infants and children and osteomalacia in adults [2]. In the most pernicious form of hypophosphatasia, the perinatal lethal variant, profound skeletal hypomineralization results in caput membranaceum with shortened and deformed limbs noted. Some affected neonates survive for several days or weeks. They often succumb to respiratory failure brought on by pulmonary hypoplasia and structural failure of the weakened skeleton from demineralization [3].

Osteoblasts modulate the composition of the bone matrix, where they deposit mineral in the form of hydroxyapatite. Specialized buds from the osteoblasts' plasma membrane are called matrix vesicles (MVs). The initiation of matrix calcification by osteoblasts and chondrocytes appears to be mediated by release of MVs, which serve as a sheltered environment for hydroxyapatite crystal formation [4-7]. MVs are alkaline phosphatase enriched, extracellular, membrane-invested bodies. Inside MVs the first crystals of hydroxyapatite bone mineral are generated. TNSALP hydrolyzes inorganic pyrophosphate ($PP_i$) to monophosphate (inorganic phosphate; $P_i$), which is important for growth of the hydroxyapatite crystal [4, 5, 8-10]. Thus ALP functions as an inorganic pyrophosphatase ($PP_i$-ase) [14, 15]. $PP_i$ itself impairs the growth of hydroxyapatite crystals as an inhibitor of mineralization [8, 11-13]. Insufficient TNSALP activity fails to hydrolyze $PP_i$ and the resulting build-up of unhydrolyzed $PP_i$ in the perivesicular matrix inhibits the proliferation of preformed hydroxyapatite crystals beyond the protective confines of MV membranes.

The level of plasma $PP_i$ increases in hypophosphatasia [16-18]. Even in the absence of TNSALP, the other phosphatases (AMPase and inorganic pyrophosphatase) can hydrolyze $PP_i$, supplying $P_i$ for incorporation into initial mineral within MVs [19] but still be insufficient to remove excess $PP_i$ at the perimeter of MVs. Thus, despite TNSALP deficiency, initial mineral could form within MVs, while its propagation into perivesicular matrix would be inhibited by a local build-up of $PP_i$ [20, 21]. These findings suggest $PP_i$ as a plausible candidate as an inhibitor of mineralization and as a primary factor that causes clinical manifestations of hypophosphatasia.

Enzyme replacement therapy (ERT) has proven effective in preventing or reversing lysosomal storage in patients and animal models with lysosomal storage diseases (LSDs) [22-28]. Tremendous progress in the development of ERT has been made in the last three decades. Cellular uptake of enzyme from the blood following intravenous administration requires specific oligosaccharides on the enzyme itself corresponding to oligosaccharide receptors on the target cells. Examples include the binding of high-mannose oligosaccharides of the enzyme to the mannose receptor (MR) and binding of phosphorylated high-mannose oligosaccharides of the enzyme to the cation-independent mannose 6-phosphate receptor (M6PR). Thus, LSDs have been considered potentially amenable to therapy with exogenously supplied enzymes.

The cell-specific delivery system was also designed to enhance the clinical effectiveness of ERT. In the case of Gaucher disease, delivery of the enzyme to the affected cells was achieved by modifying the N-linked carbohydrate on the enzyme. This exposed core mannose residues [29, 30], enabling the enzyme to bind to the MR, which is highly abundant on cells of the reticuloendothelial system [31, 32]. These findings led to clinical management of Gaucher disease by ERT [22]. Over 3,500 patients have been treated with dramatic clinical results [33].

However, hypophosphatasia caused by a deficiency of TNSALP seems to be a difficult disorder treated by ERT because TNSALP is a membrane-bound enzyme and is believed to require attachment at the cell surface to be functional. In fact, the results of multiple intravenous infusions of plasma ALP or purified liver ALP in patients with hypophosphatasia have been disappointing [34-38]. Administration of exogenous pyridoxal HCl delayed the onset of epileptic attacks and increased the life span of TNSALP−/− mice. Although the oldest survivor was 22 days old, all the homozygotes, however, died near weaning time, irrespective of their treatment regime [39].

The inventors have genetically engineered a Chinese Hamster Ovarian (CHO) cell line to produce a C-terminus-anchorless TNSALP enzyme, in secreted form, [40] and showed clinical effectiveness of ERT on hypophosphatasia mice. These results indicate that the C-terminus-anchorless membrane enzyme possesses the characteristics necessary for use in ERT where the membrane-binding form is ineffective. Deletion of the C-terminus membrane anchor will be applicable to other membrane-binding proteins whose deficiency leads to other human disorders including but not limited to paroxysmal nocturnal haemoglobinuria (PNH).

Targeted therapies have the advantage of reducing adverse effects on non-target organs as well as reducing the minimum effective systemic dose. Recently, Kasugai et al [41] has demonstrated that a small peptide consisting of a stretch of acidic amino acids (L-Aspartic acid or L-Glutamic acid) was selectively delivered to and retained in bone after a systemic administration. Furthermore, a small molecule, an estrogen, conjugated with an acidic-oligopeptide, has been selectively targeted to bone, leading to dramatic improvement of the bone mineral density in ovariectomized mice with no or few adverse effects to liver and uterus [42]. However, whether such a bone-targeting system with an acidic oligopeptide could be applied to a large molecule such as an enzyme in a manner such that the enzyme is functional and efficiently produced remains unsolved.

The inventors have sought to address the issue of enzyme replacement therapy using membrane bound enzymes genetically modified to be synthesized in an active secretory form. In particular the inventors have applied this method to TNSALP as a treatment for hypophosphatasia. This method of releasing membrane bound enzymes in a functional form will offer new avenues for therapeutic strategies to combat disease of enzyme deficiency.

SUMMARY OF THE INVENTION

The inventors have made the surprising discovery that removal of the nucleotide sequence encoding the C-terminus glycosylphosphatidylinositol (GPI) anchoring signal peptide of a membrane bound enzyme and expressing that nucleotide sequence in a host cell, will result in the synthesis and extracellular release of an active enzyme in a soluble form. Furthermore, a membrane bound enzyme such as tissue-nonspecific alkaline phosphatase (TNSALP) in an anchorless form is useful in enzyme replacement therapy for treatment of hypophosphatasia.

Hypophosphatasia, caused by deficient activity of TNSALP results in defective bone mineralization. Plasma infusions of TNSALP have not achieved clinical improvement. No definitive treatment is presently available. Enzyme replacement therapy for hypophosphatasia was not thought to be feasible since TNSALP exists as a membrane-bound enzyme and functions physiologically when the enzyme is present at the cell membrane. A tissue TNSALP knock-out mouse provides a model of infantile hypophosphatasia displaying impaired bone mineralization, epileptic seizures, apnoea, and abnormal apoptosis in the thymus, abnormal lumbar nerve roots, and postnatal death before the weaning.

To investigate the clinical effectiveness of ERT for hypophosphatasia, the inventors deleted the C-terminus of TNSALP cDNA encoding the GPI anchoring signal peptide sequence and transfected the modified nucleotide into the Chinese hamster ovary (CHO) cell line. The result was a secreted form of anchorless recombinant human TNSALP (anchorless rhTNSALP) produced by CHO cells, which was subsequently purified and characterized in vitro.

An in vivo study was carried out, which utilized weekly infusions of anchorless rhTNSALP into TNSALP knockout mice. In vitro mineralization assays with anchorless rhTNSALP in the presence of high concentrations of pyrophosphate provided evidence of bone mineralization with bone marrow from a hypophosphatasia patient. Administration of the purified anchorless rhTNSALP enzyme into TNSALP knockout mice increased life span and increased body weight, showing that the treated mice lived approximately 4 and 7 times longer compared to the untreated mice. Treated mice had no epileptic seizures until at least 3 months old.

These results show the C-terminus anchorless rhTNSALP functions bioactively in vivo and that is a good candidate for ERT for hypophosphatasia. This invention can be applied to other diseases deficient in membrane-bound proteins.

Targeted therapies are often advantageous because they can reduce overall total effective dose and in turn adverse consequences to patients. To this purpose the inventors tagged anchorless rhTNSALP enzymes with an acidic oligopeptide, of six or eight residues of L-Aspartic acid, to provide high affinity binding to hydroxyapatite which is abundant in bone. The inventors characterized the biochemical properties of the purified tagged enzymes in comparison with the untagged enzyme to evaluate the feasibility of bone-directional delivery. CHO cell lines were established producing the tagged anchorless rhTNSALP enzymes as a secreted form. It was found that specific activities of the purified enzymes tagged with the acidic oligopeptide were almost the same as the untagged enzyme. In vitro affinity measurements indicated that the poly-aspartic acid tagged enzymes had an approximately 10-fold higher affinity to hydroxyapatite than the untagged TNSALP enzyme. Lectin affinity chromatography showed little difference among the tagged and untagged enzymes in carbohydrate structure except the tagged enzymes had fewer sialic acid residues. Biodistribution pattern analysis by infusion of the fluorescence-labeled enzymes into mice showed that the amount of the tagged enzymes retained in bone was 4-fold higher than that of the untagged enzyme at 6 hours post-infusion. The tagged enzymes were retained at higher levels continuously up to one week.

These results indicate that the enzymes tagged with an acidic oligopeptide are delivered more specifically to bone and possess a high affinity for hydroxyapatite, suggesting the potential use of the tagged enzymes in targeted ERT for hypophosphatasia.

Therefore, an object of this invention is a method of modifying a membrane bound protein by eliminating the GPI anchor such the protein is not bound to the cell membrane and may exist extracellularly in a soluble active form.

In another embodiment, the object of this invention is a TNSALP, modified so that it does not comprise a GPI anchor, and that this anchorless TNSALP is not bound to the cell membrane and may exist extracellularly in a soluble active form such that it may be used therapeutically in enzyme replacement therapy for ALP deficient diseases such as hypophosphatasia.

In another embodiment, the object of this invention is a TNSALP, modified such that the TNSALP does not comprise a GPI anchor and this anchorless TNSALP is not bound to the cell membrane and may exist extracellularly in a soluble active form, and further comprises an acidic oligopeptide sequence, such as poly-aspartic acid, providing a high affinity for bone tissue so that it may be used therapeutically in ERT for ALP deficient diseases such as hypophosphatasia.

In another embodiment, the invention is drawn to a method of manufacturing an ALP ERT factor, comprising the steps of a) deleting the GPI anchor signal peptide encoding sequence form a nucleotide, b) transfecting a cell with said modified nucleotide, c) culturing the cell, and d) purifying the ALP ERT factor form the culture media.

In yet another embodiment the invention is drawn to a method of treating a patient with hypophosphatasia using ALP ERT factors.

It is envisioned that the instant ALP ERT factors (supra) may be administered to patients in vivo, in a pharmaceutically acceptable formulation as a therapy for the treatment of hypophosphatasia, or encoded a nucleotide sequence to be expressed in cells within a patient to supply the aforementioned factors.

DETAILED DESCRIPTION OF THE INVENTION

Figure 1:
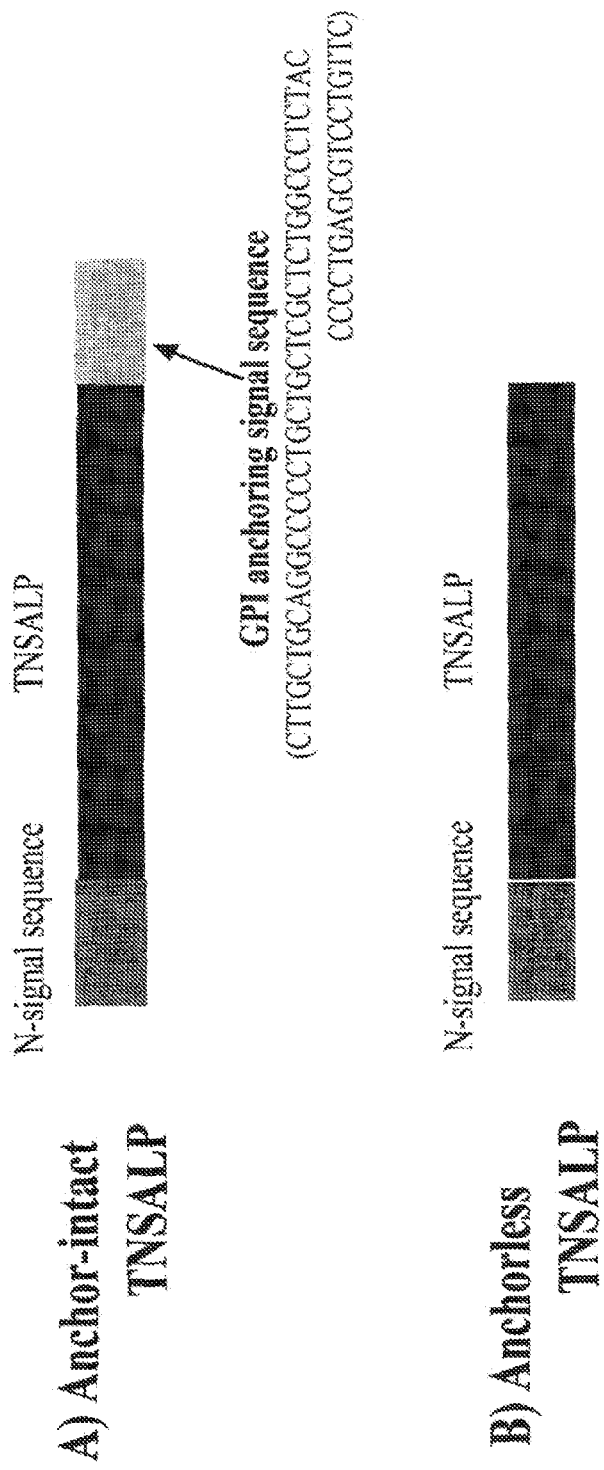
FIG. 1 Construct of anchorless TNSALP. The glycosylphosphatidylinositol (GPI) anchoring signal peptide sequence of TNSALP (SEQ ID NO: 2) was deleted from (A) the full-length of TNSALP cDNA to produce (B) cDNA encoding the secreted form of the enzyme.

In vivo, TNSALP is bound to plasma membranes by a GPI anchor, which is added after removal of a C-terminus peptide during post-translational processing. TNSALP functions as an ectoenzyme. In this study, the inventors have removed the nucleotide sequence encoding the GPI anchor signal from human TNSALP cDNA in order to express and secrete an anchorless form of TNSALP into the culture medium of overexpressing CHO-K1 cells. This study demonstrates that removal of the GPI anchoring signal peptide sequence from the C-terminus of TNSALP cDNA allows the overexpressing CHO-K1 cells to produce sufficient amounts of recombinant human enzyme in a secreted form, and that this anchorless recombinant human TNSALP enzyme is bioactive and able to initialize bone mineralization in bone marrow from hypophosphatasia patients. In addition, when anchorless rhTNSALP was infused into the sublethal form of TNSALP (−/−) mouse, it improved clinical features and increased both life span and growth, further indicating the feasibility of enzyme replacement therapy for hypophosphatasia.

Hypophosphatasia is a metabolic bone disease that establishes an important role for alkaline phosphatase (ALP) in skeletal mineralization. Subnormal serum ALP activity (hypophosphatasemia) constitutes the biochemical hallmark and reflects a generalized deficiency of activity of the tissue-nonspecific (liver/bone/kidney) ALP isoenzyme (TNSALP). Activities of the three tissue-specific ALP isoenzymes in humans—intestinal, placental, and germ-cell (placental-like) ALP—are not diminished. TNSALP is a zinc metalloglycoprotein that is catalytically active as a multimer of identical subunits. It is bound to plasma membranes by GPI linkage.

Hypophosphatasia is characterized clinically by defective skeletal mineralization that manifests as rickets in infants and children and osteomalacia in adults. Clinical expressivity is, however, extremely variable. Stillbirth can occur from in utero onset in the perinatal ("lethal") form, which is apparent in newborns and associated with the most severe skeletal hypomineralization and deformity. The infantile form presents as a developmental disorder by age 6 months. It may cause craniosynostosis and nephrocalcinosis from hypercalcemia and hypercalciuria and is often fatal. Premature loss of deciduous teeth and rickets are the cardinal clinical features of childhood hypophosphatasia. Adult hypophosphatasia typically results in recurrent metatarsal stress fractures and pseudofractures in long bones and occasionally produces arthritis from calcium pyrophosphate dihydrate (CPPD) and perhaps calcium phosphate crystal deposition. Odontohypophosphatasia refers to especially mildly affected individuals who have dental, but no skeletal, manifestations.

Three phosphocompounds [phosphoethanolamine (PEA), PPi, and pyridoxal 5'-phosphate (PLP)] accumulate endogenously in hypophosphatasia and are inferred to be natural substrates for TNSALP. A variety of evidence shows that PLP, a cofactor form of vitamin B6, collects extracellularly; intracellular levels of PLP are normal. This observation explains the absence of symptoms of deficiency or toxicity of vitamin B6 and indicates that TNSALP functions as an ectoenzyme. Extracellular accumulation of PPi, which at low concentrations promotes calcium phosphate deposition but at high concentrations acts as an inhibitor of hydroxyapatite crystal growth, appears to account for the associated CPPD deposition and perhaps calcific periarthritis, as well as the defective mineralization of bones and teeth. There is no established medical treatment. Enzyme replacement by IV infusion of ALP from various tissue sources has generally not been of significant clinical benefit [34-38]. Therefore, it has long been thought that since TNSALP is a membrane-bound protein, via GPI linkage, TNSALP needs to be attached to the membrane to provide a physiological function.

In this study the inventors have established a newly designed ERT for hypophosphatasia with C-terminus anchorless recombinant human TNSALP and have shown clinical effectiveness with the TNSALP (−/−) mouse model. This strategy is applicable to other GPI-anchored proteins whose dysfunction leads to the human disorders such as paroxysmal nocturnal haemoglobinuria (PNH) and prion diseases.

Bone Targeted Anchorless rhTNSALP

The development of selective drug delivery to bone will enhance the clinical effectiveness of bioactive enzymes used in ERT. To this purpose, the inventors have invented an acidic-oligopeptide-tagged bone-directional anchorless rhTNSALPs for use in ERT, and have characterized these enzymes for their bone-targeting properties. The inventors tagged the anchorless rhTNSALP enzymes with an acidic oligopeptide (a six or eight stretch of L-Aspartic acid), to provide a high affinity for hydroxyapatite, which is abundant in bone. The inventors characterized the biochemical properties of the purified tagged enzymes in comparison with the untagged enzyme to evaluate the feasibility of the bone-directional delivery.

CHO cell lines producing tagged (six or eight residues of L-Aspartic acid) and untagged anchorless rhTNSALP enzymes were established. The specific activity of purified enzymes tagged with the acidic oligopeptides was almost identical with the untagged enzyme. In vitro affinity assays showed that the tagged anchorless rhTNSALPs had a 10-fold higher affinity for hydroxyapatite than the untagged anchorless rhTNSALP. Lectin affinity chromatography showed little difference in carbohydrate structure among the tagged and untagged enzymes except for fewer sialic acid residues on the tagged enzymes. The examination of biodistribution patterns after a single infusion of fluorescence-labeled ALP ERT factors into mice showed that the amount of tagged enzymes retained in bone were 4-fold higher than that of the untagged enzyme at 6 hours post-infusion. The tagged enzymes were retained continuously at a higher level up to one week.

These results show that ALP ERT factors tagged with an acidic oligopeptide are characterized with a more specific affinity binding to the hydroxyapatite, suggesting the potential use of the tagged enzymes for ERT on hypophosphatasia.

Therefore, the invention is drawn to (1) a method of producing an anchorless membrane bound protein in a soluble active form, by deleting the GPI anchoring signal peptide, (2) composition and manufacture of an anchorless human recombinant TNSALP (anchorless rhTNSALP) for treatment of hypophosphatasia by deleting the GPI anchoring signal peptide nucleic acid sequence from cDNA and transfecting a host cell for high yield expression and release of the enzyme, (3) a method and composition for an acidic oligopeptide tagged variant of anchorless rhTNSALP for targeted delivery to bone, and (4) methods of using anchorless rhTNSALP and oligopeptide tagged variants of anchorless rhTNSALP to treat hypophosphatasia in a patient.

The term "anchorless recombinant human TNSALP" or "anchorless rhTNSALP" refers to the tissue non-specific alkaline phosphatase (TNSALP) which has been modified by deletion of the GPI anchor. The term "TNSALP" generally referees to tissue non-specific alkaline phosphatase. As used in FIGS. 1, 3, 6, and 8 as well as the provisional application to which this application claims priority, TNSALP or rhTNSALP, where it is applicably described, is equivalent to, anchorless human recombinant TNSALP or anchorless rhTNSALP.

The terms "CD6-TNSALP" and "CD8-TNSALP" or "CD6" and "CD8" refer to the anchorless recombinant human TNSALP or anchorless rhTNSALP which have been tagged with 6 or 8 L-aspartic acid residues attached at the carboxyl terminus respectively. The term "tagged" or "oligopeptide tagged" means the act of adding to, in this case, referring to the adding of six or eight aspartic acids residues to anchorless rhTNSALP through genetic engineering or other chemical means.

The term "ALP" refers to the family of alkaline phosphatase enzymes generally.

The term "ERT" refers to enzyme replacement therapy for treatment of disease. A disease caused by enzyme deficiency treated through replacement of the deficient enzyme. As used here it refers to replacement of the deficient enzyme, by way of explanation but not of limitation, inter venous infusion or administration of a corrective gene or cell containing a corrective gene to produce the deficient enzyme in a patient.

The term "ALP ERT factors" refers generally to alkaline phosphatase enzymes useful in enzyme replacement therapy. More specifically this term is meant to include all compositions of anchorless rhTNSALP, CD6-TNSALP and CD8-TNSALP disclosed herein.

The term "GPI anchor" is meant to refer to glycosylphosphatidylinositol attached at or near the C-terminus of a membrane bound protein, thereby binding the membrane bound protein to the membrane via its lipidphilic affinity with the membrane.

The term "GPI anchor signal peptide" is meant to refer to the C-terminus amino acid sequence recognized during post-translational processing as a single for adding GPI and thereby anchoring the protein.

The term "GPI anchor single peptide sequence" refers to a nucleotide sequence encoding the GPI anchor signal peptide.

The term "active" means a functional state of a molecule where it performs as it would in vivo, including reactions the enzymes is know to facilitate or binding or blocking functions receptors may be know to possess. Active also includes any pro-active state, pro-enzymes which normally exist in a precursor from; that is not capable of carrying out their known function until activated by another factor or co-factor.

Sequence identity or percent identity is intended to mean the percentage of same residues between two sequences. The two reference sequences used are the entire peptide sequence of human tissue non-specific alkaline phosphatase precursor (residues 1-524), or the GPI anchor single peptide of human tissue non-specific alkaline phosphatase precursor (residues 506-524). In all sequence comparisons, the two sequences being compared are aligned using the Clustal method (Higgins et al, Cabios 8:189-191, 1992) of multiple sequence alignment in the Lasergene biocomputing software (DNASTAR, INC, Madison, Wis.). In this method, multiple alignments are carried out in a progressive manner, in which larger and larger alignment groups are assembled using similarity scores calculated from a series of pairwise alignments. Optimal sequence alignments are obtained by finding the maximum alignment score, which is the average of all scores between the separate residues in the alignment, determined from a residue weight table representing the probability of a given amino acid change occurring in two related proteins over a given evolutionary interval. Penalties for opening and lengthening gaps in the alignment contribute to the score. The default parameters used with this program are as follows: gap penalty for multiple alignment=10; gap length penalty for multiple alignment=10; k-tuple value in pairwise alignment=1; gap penalty in pairwise alignment=3; window value in pairwise alignment=5; diagonals saved in pairwise alignment=5. The residue weight table used for the alignment program is PAM250 (Dayhoff et al., in Atlas of Protein Sequence and Structure, Dayhoff, Ed., NBRF, Washington, Vol. 5, suppl. 3, p. 345, 1978).

TABLE 1

Percent Identity of ALPs.

| Species | Accession number | Percent Identity |
|---|---|---|
| Human tissue non-specific alkaline phosphatase precursor | NP_000469 | 100 |
| Rhesus tissue non-specific alkaline phosphatase | XP_001109717 | 97 |
| Rat tissue-nonspecific alkaline phosphatase | NP_037191 | 90 |
| Dog tissue non-specific alkaline phosphatase | AAF64516 | 89 |
| Pig alkaline phosphatase | AAN64273 | 88 |

Shown are calculations of percent identity for comparison of alkaline phosphatase from various mammalian species relative to human tissue non-specific alkaline phosphatase precursor.

TABLE 2

Percent Identity of GPI anchor single peptide.

| Species | Accession number | Percent Identity |
|---|---|---|
| Human tissue non-specific alkaline phosphatase precursor (residues 506-524) | NP_000469 | 100 |
| Rhesus tissue non-specific alkaline phosphatase residues (634 652) | XP_001109717 | 84 |
| Pig alkaline phosphatase (residues 237-253) | AAN64273 | 75 |
| Dog tissue non-specific alkaline phosphatase (residues 487-502) | AAF64516 | 68 |
| Rat tissue-nonspecific alkaline phosphatase (residues 509-524) | NP_037191 NP_599169 | 68 |

Shown are calculations of identity for comparisons of GPI anchor single peptide sequences from various mammalian species relative to the GPI binding signal peptide of human tissue non-specific alkaline phosphatase precursor.

Preferred embodiments of the invention are described in the following examples. Other embodiments within the scope of the claims herein will be apparent to one skilled in the art from consideration of the specification or practice of the invention as disclosed herein. It is intended that the specification, together with the examples, be considered exemplary only, with the scope and spirit of the invention being indicated by the claims, which follow the examples.

Example 1

Preparation and Biochemical Characterization of Enzymes

The GPI anchoring signal peptide was removed from the carboxyl-terminal of the human TNSALP to release the enzyme in the media of CHO-K1 cells. This was accomplished by deleting the GPI anchoring signal sequence from full length TNSALP cDNA (FIG. 1). The resultant anchorless rhTNSALP enzyme (>95%) was mainly secreted to culture medium in a transient expression study (data is not shown). Acidic oligopeptide-tagged enzymes (CD6-TNSALP and CD8-TNSALP), which also lack the GPI anchoring signal peptide, were secreted in to the culture medium as well. Constructs for the CD6- to CD8-TNSALP cDNA were made and transfected into CHO-1 cells for transient expression. Cells stably expressed and secreted active TNSALP enzymes into the medium in linear fashion for 12 h. However expression of enzyme plateaued after 12 hours. The inventor's previous work with oligopeptide-tagged enzymes showed that increasing the number of Aspartic acid residues beyond eight caused a substantial reduction of enzyme activity secreted into culture media in the transient expression (data not shown). The inventors chose the 6 and 8 aspartic acid tagged enzymes (CD6-TNSALP and CD8-TNSALP) for further evaluation as their experience had shown that these molecules will exhibit superior expression characteristics.

The purification of these enzymes was performed by a two-step column chromatography method, using DEAE-Sepharose and Sephacryl S-400, as summarized in Table 3. The overall purification yields of anchorless rhTNSALP, CD6-TNSALP, and CD8-TNSALP were 32%, 62%, and 56% of the total enzymes in the culture media, respectively, and the specific activities of each enzyme were 2744, 2411, and 2374 units/mg, respectively. The lower purification yield of anchorless rhTNSALP than those of the tagged enzymes was apparently due to a broader peak eluted from the DEAE column.

TABLE 3

Purification of rhTNSALP and acidic oligopeptide-tagged TNSALP from condition medium

| | Protein concentration (mg/l) | Total protein (mg) | Total activity (units) | Specific activity (units/mg) | Purification | Yield |
|---|---|---|---|---|---|---|
| | rhTNSALP | | | | | |
| Crude media | 5.26 | 115 | 3003 | 26.1 | 1 | 100 |
| DEAE column | 18.3 | 0.66 | 1555 | 2354 | 90 | 52 |
| Sephacryl S-400-HR Column | 15.4 | 0.35 | 973 | 2744 | 105 | 32 |
| | CD6-TNSALP | | | | | |
| Crude media | 6.27 | 127 | 3022 | 23.9 | 1 | 100 |

TABLE 3-continued

Purification of rhTNSALP and acidic oligopeptide-tagged TNSALP from condition medium

| | Protein concentration (mg/l) | Total protein (mg) | Total activity (units) | Specific activity (units/mg) | Purification | Yield |
|---|---|---|---|---|---|---|
| DEAE column | 32.3 | 1.01 | 2073 | 2043 | 86 | 69 |
| Sephacryl S-400-HR Column | 22.1 | 0.77 | 1862 | 2711 | 101 | 62 |
| CD8-TNSALP | | | | | | |
| Crude media | 3.85 | 184 | 3065 | 16.6 | 1 | 100 |
| DEAE column | 29.1 | 1.00 | 2028 | 2035 | 123 | 66 |
| Sephacryl S-400-HR Column | 22.4 | 0.72 | 1702 | 2374 | 143 | 56 |

Figure 2:
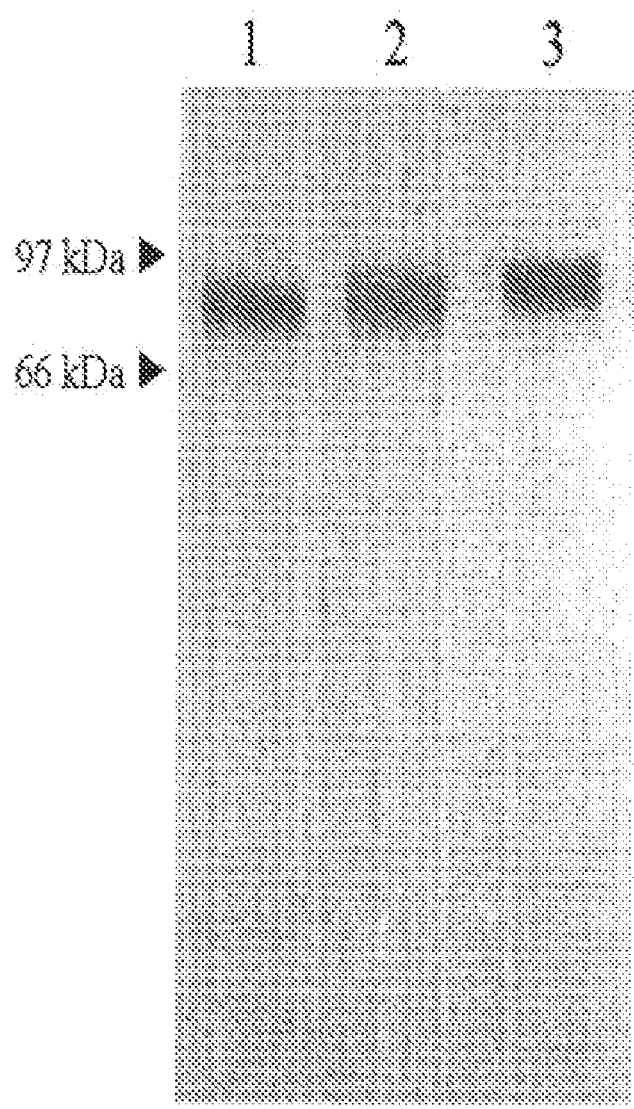
FIG. 2. SDS-PAGE of ALP ERT factors from condition medium. The purified enzymes (0.2 μg) were subjected to SDS-PAGE under reducing condition and stained with silver. A Single band appeared in all the three enzymes. The molecular mass of the untagged anchorless rhTNSALP (lane 1) was approximately 80 kDa, while those of CD6- and CD8-TNSALP were larger (lanes 2 and 3, respectively).

When the purified anchorless rhTNSALP was subjected to SDS-PAGE under reducing conditions, a single band with approximately 80 kDa of molecular mass was detected (FIG. 2). An increase of molecular mass associated with an additional acidic oligopeptide was observed in CD6- and CD8-TNSALP.

There was little difference among anchorless rhTNSALP, CD6-TNSALP, and CD8-TNSALP in Michaelis constant (KM), as defined by the pNPP substrate with double-reciprocal plots (0.37, 0.39, and 0.37 mM, respectively), or in chemical inhibition by L-phenylalanine (10 mM; 83%, 86%, and 86% of remaining enzyme activity, respectively) and L-homoarginine (10 mM; 12%, 13%, and 12% of remaining enzyme activity, respectively).

Example 2

Characteristics of Poly-Aspartic Acid—Tagged Anchorless rhTNSALP

Affinity for Hydroxyapatite

Figure 3:
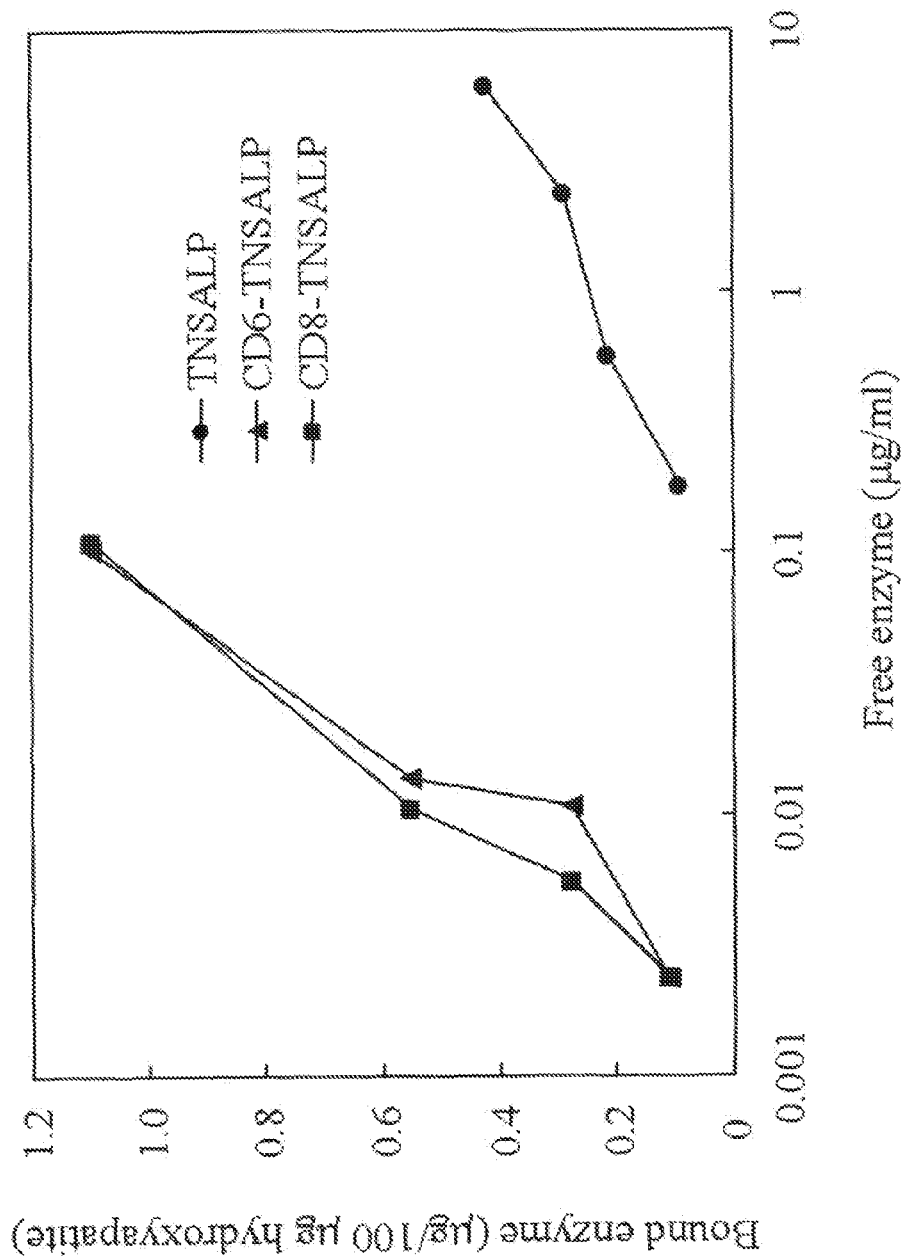
FIG. 3. Concentration-dependent binding curves of anchorless TNSALP and tagged anchorless TNSALP to hydroxyapatite. Purified enzymes were mixed with a hydroxyapatite suspension at a final concentration of 1.0, 2.5, 5.0, and 10.0 μg/ml. The mixture was mixed at 37° C. for 1 h, and centrifuged at 14,000×rpm for 10 min to separate bound and unbound enzymes. To determine the amount of the unbound enzyme, the enzyme activity in supernatant was measured. The amount of bound enzyme was determined by measuring both total and unbound enzymes. Affinity for hydroxyapatite for oligo Aspartic acid tagged enzymes was 10-fold higher than that for the untagged enzyme. Also binding to hydroxyapatite was seen at lower concentrations of Aspartic acid tagged enzyme.

A remarkable difference between the tagged and untagged enzymes was observed in their affinity to hydroxyapatite. Affinity to hydroxyapatite for the tagged enzymes was 10-fold higher than that for the untagged enzyme and the binding to hydroxyapatite was seen even at low concentration of the tagged enzyme (FIG. 3). The binding parameters, $K_b$ and $B_{max}$, are shown in Table 4. The values of $K_b$ and $B_{max}$ of the tagged enzymes were 10- and 3-fold, respectively, higher than those of the untagged enzyme. Although no significant difference was observed between CD6- and CD8-TNSALP.

TABLE 4

Binding parameters of three enzymes to hydroxyapatite.

| | $K_b$ ($ug^{-1}$ml) | $B_{max}$ (ug/100 ug hydroxyapatite) |
|---|---|---|
| rhTNSALP | 1.7 ± 1.0 | 0.5 ± 0.2 |
| CD6-TNSALP | 36.7 ± 7.9 | 1.6 ± 0.3 |
| CD8-TNSALP | 44.6 ± 4.6 | 1.9 ± 0.7 |

Each value represents the mean ± S.D. of 3 experiments. $K_b$ binding constant and $B_{max}$ maximum binding rates were determined form double-reciprocal plots.

Elution Profiles of Enzymes by Lectin Affinity Chromatography

Figure 4:
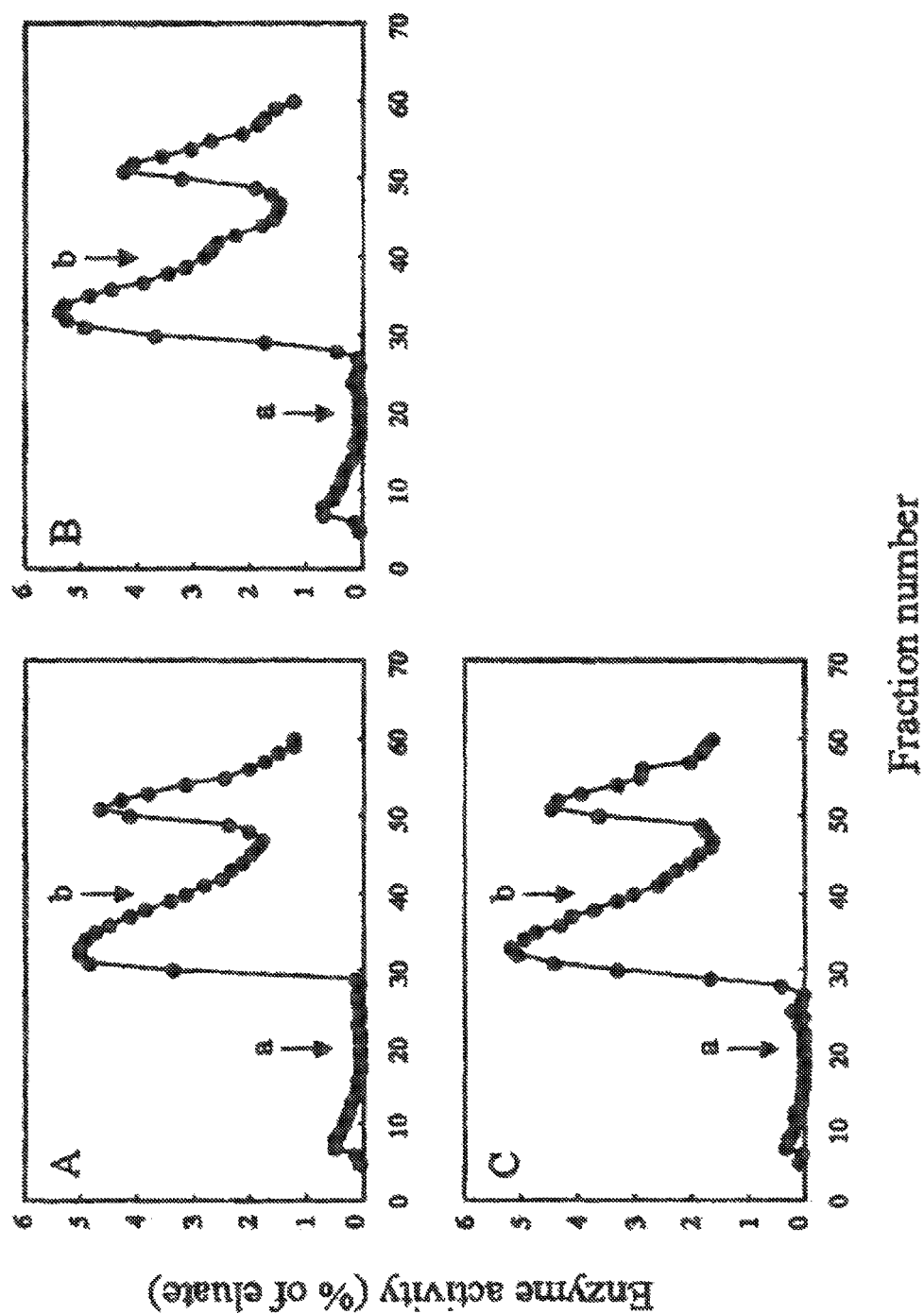
FIG. 4. ConA affinity chromatography of three ALP ERT factors. Anchorless rhTNSALP (A), CD6-TNSALP (B), and CD8-TNSALP (C) were applied to a ConA affinity column. After washing the column, two fractions were eluted by two different concentrations, 0.01 M (arrow; a) and 0.5 M (arrow; b) of αMM. There was no difference in the elution profile among the three enzymes.
Figure 5:
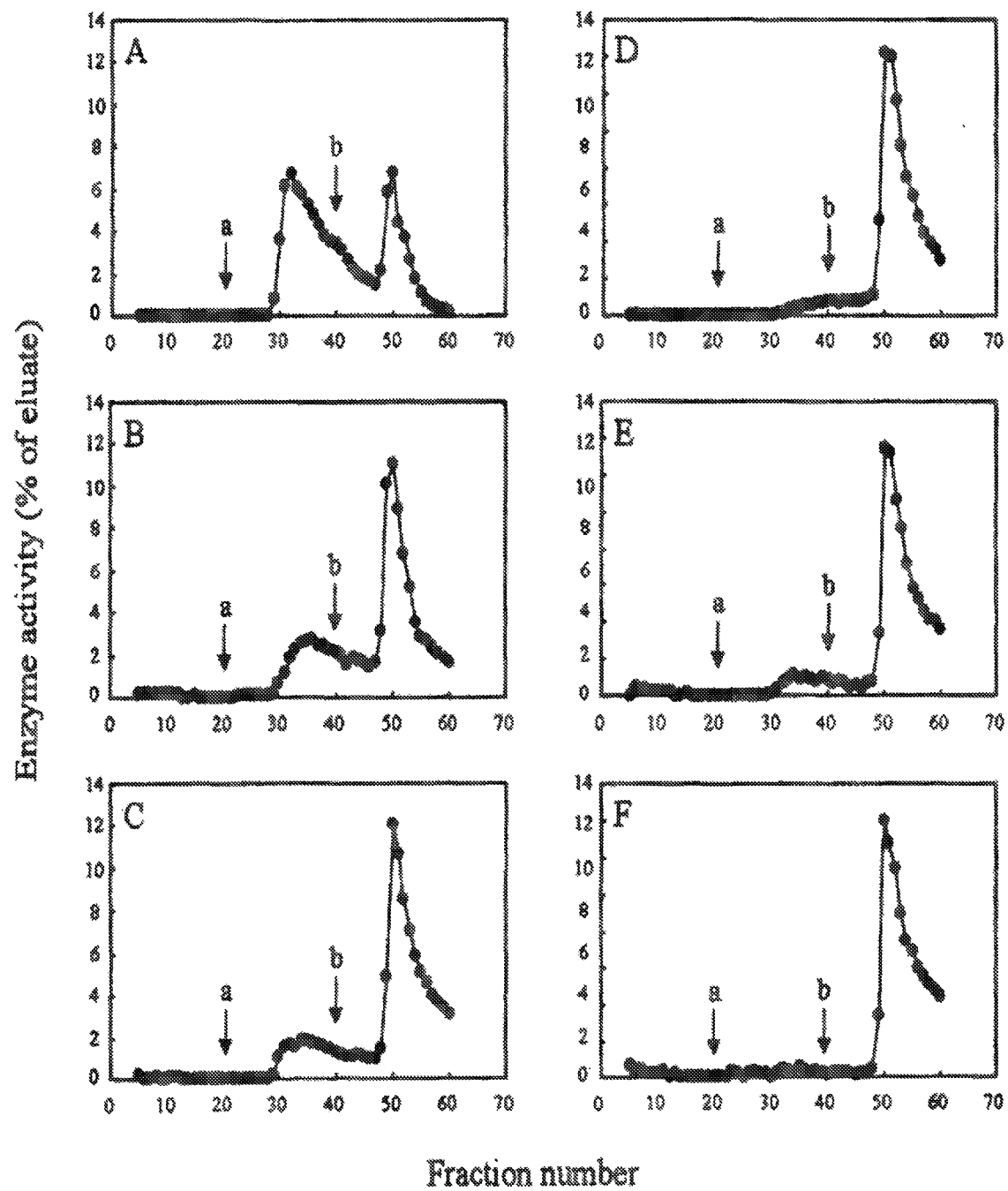
FIG. 5. WGA affinity chromatography of ALP ERT factors. ALP ERT factors before (A-C) and after (D-F) the neuraminidase digestion were applied to the WGA affinity chromatography. The anchorless rhTNSALP (A and D), CD6-TNSALP (B and E), and CD8-TNSALP (C and F) enzymes were applied to the WGA column. After washing the column, two fractions were eluted by the two different concentrations, 0.1 M (arrow; a) and 0.5 M (arrow; b) of GlcNAc.

Three enzymes, rhTNSALP, CD6-, and CD8-TNSALP, were subjected to ConA affinity chromatography. (FIG. 4). ConA affinity chromatography indicated there was little unbound enzyme, whereas weakly-bound and strongly-bound enzymes were detected. Overall the elution profiles of these enzymes did not differ when two different concentrations of competitive sugars were added. Since ConA has a high reactivity to the mannosyl residues, the inventors concluded that these enzymes did not differ with respect to mannosyl residue composition. In contrast, the WGA elution profiles between the tagged and untagged enzymes were remarkably different in the ratio of strongly-bound enzyme and weakly-bound enzyme (FIG. 5A-C). Table 5 shows the percentages of the relative enzyme activity of three fractions on the WGA column. Approximately 30% of the tagged enzymes were weakly bound and 70% was strongly bound to the WGA column, while 66% of the untagged enzyme was weakly bound and 34% was strongly bound to the WGA column. The content of the weakly-bound enzyme was larger in the order of rhTNSALP>CD6-TNSALP>CD8-TNSALP.

TABLE 5

Percentage of Unbound, Weakly bound, and Strongly bound fractions obtained by each ConA and WGA column

| | Percent of relative activities | | | | | | | | |
|---|---|---|---|---|---|---|---|---|---|
| | ConA | | | WGA | | | WGA + Neuraminidase | | |
| | rhTNSALP | CD6 | CD8 | rhTNSALP | CD6 | CD8 | rhTNSALP | CD6 | CD8 |
| Unbound | 3 | 4 | 2 | 0 | 3 | 1 | 0 | 2 | 4 |
| Weakly Bound | 59 | 60 | 59 | 66 | 32 | 23 | 9 | 11 | 4 |
| Strongly Bound | 38 | 36 | 39 | 33 | 65 | 76 | 91 | 86 | 92 |

Figure 6:
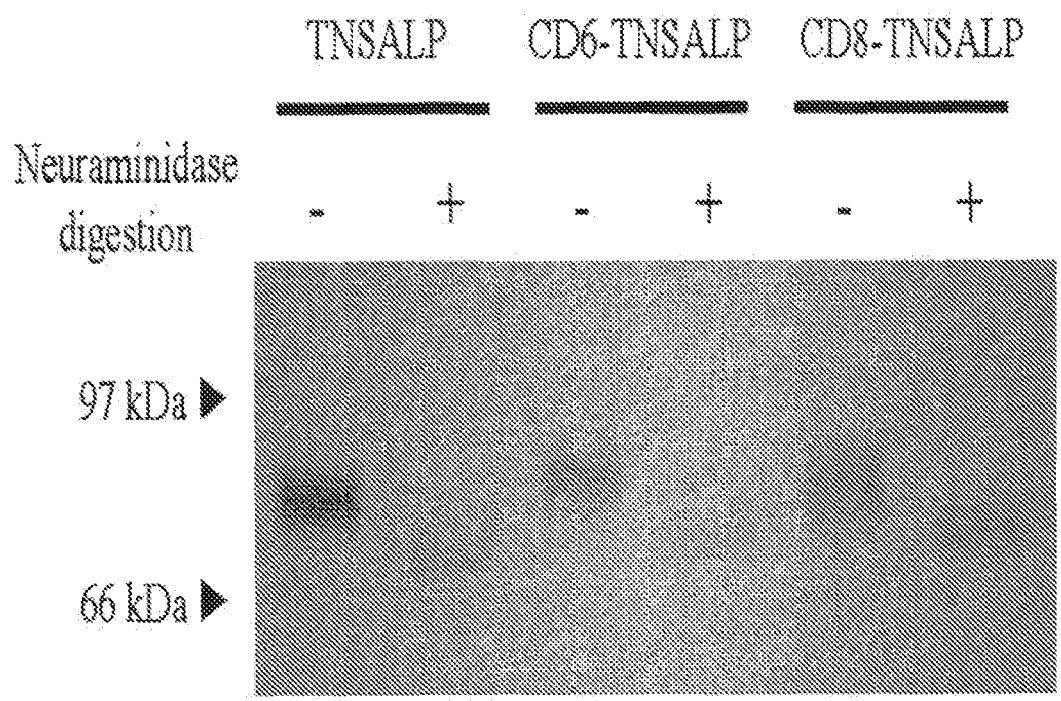
FIG. 6. SDS-PAGE of ALP ERT factors before and after neuraminidase digestion. The enzymes (0.3 μg) were subjected to SDS-PAGE under reducing condition and stained with silver. A single band was observed at all the lanes. After the treatment with neuraminidase, the molecular mass of the three enzymes decreased in a similar proportion.

To estimate the content of the sialic acid residues of the enzyme, we treated three enzymes with neuraminidase thereby removing the sialic acid residues from the enzymes. After the treatment with neuraminidase, the molecular masses of three enzymes decreased in a similar proportion (FIG. 6). The elution profile of the untagged enzyme on the WGA column changed after the neuraminidase digestion. The earlier fraction accounting for the weakly-bound enzyme shifted to the later fraction for the highly-bound enzyme (FIG. 5D). On the other hand, the elution profiles of the tagged enzymes on the WGA column slightly changed with neuraminidase digestion (FIGS. 5E and 5F), since the tagged enzymes originally included a less amount of weakly-bound enzyme.

Biodistribution of Fluorescence-Labeled Enzymes

Figure 7:
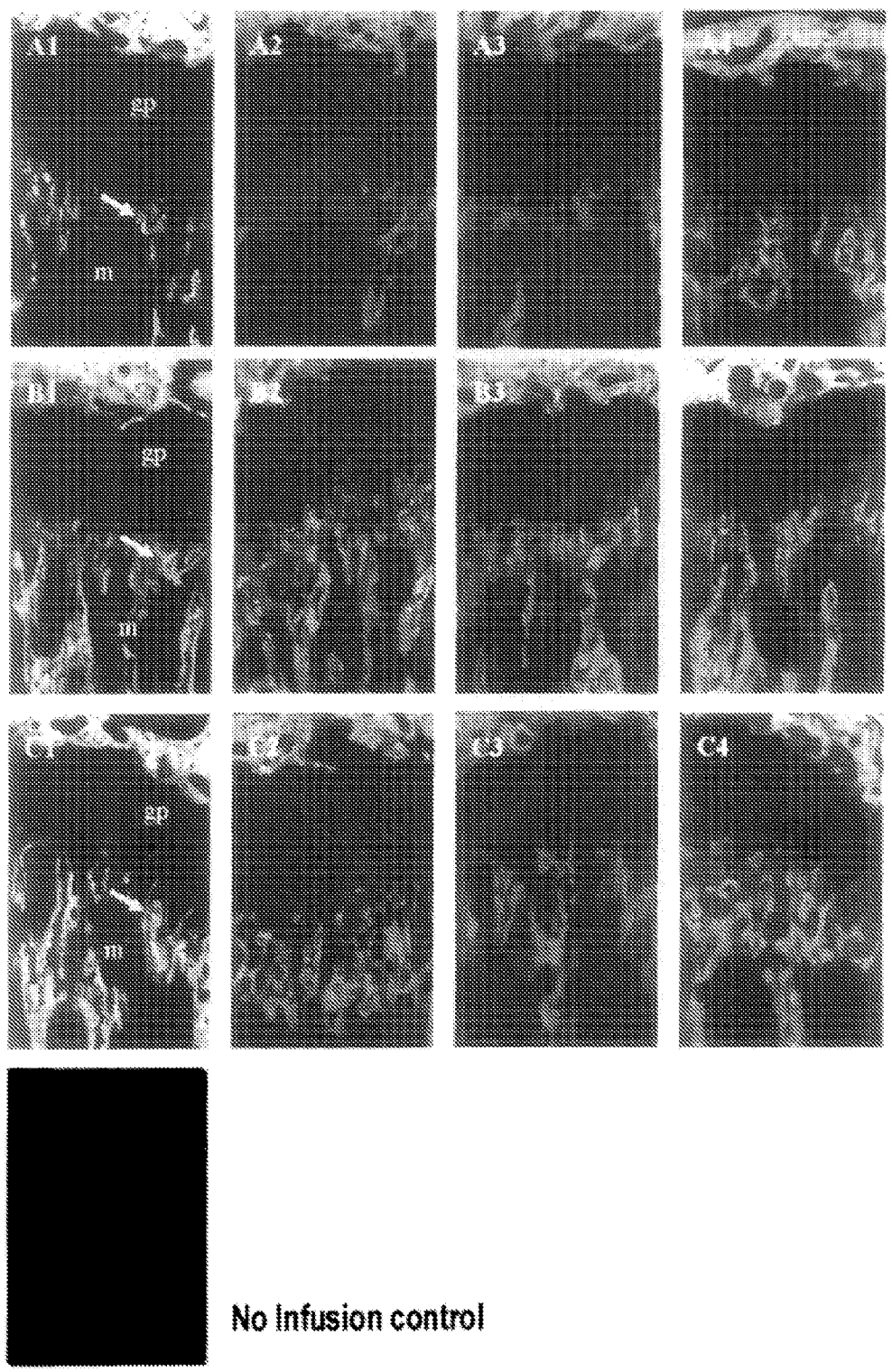
FIG. 7. Biodistribution of fluorescence-conjugated ALP ERT factors to bone. Fluorescence-labeled ALP ERT factors, (A) anchorless rhTNSALP, (B) CD6-TNSALP, and (C) CD8-TNSALP, were infused to mice from tail vein at the dose of 1 mg/kg of body weight. At the indicated time points 6, 24, 72, and 168 hours (1, 2, 3, and 4 respectively), the legs were dissected and sectioned. The sections of legs were observed under a fluorescent microscopy to evaluate the enzyme distribution at the epiphyseal region. ALP ERT factors were distributed to the mineralized region (m), but not to the, growth plate (gp).
Figure 8:
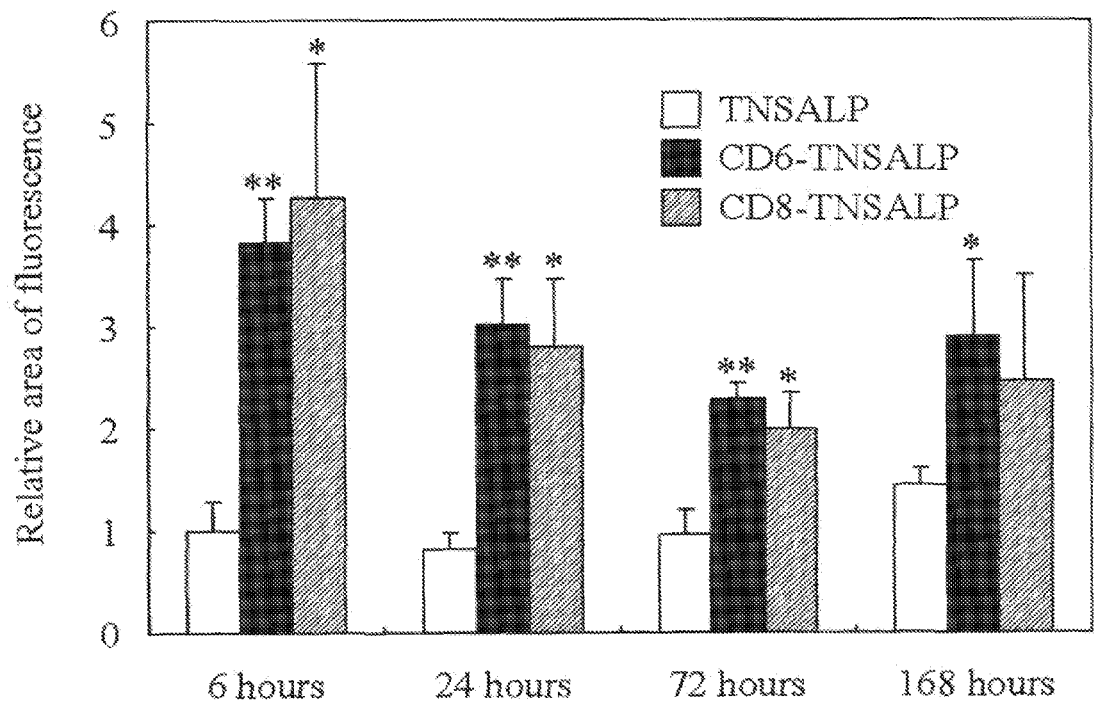
FIG. 8. Relative area of fluorescence around growth plate after a single infusion of fluorescence-ALP ERT factors. The average of the relative areas of fluorescence from three fields of the fluorescent images at epiphyseal region was quantitated.

To evaluate the pharmacokinetic tissue distribution pattern of these enzymes, the fluorescence-labeled enzymes were prepared by the Alexa dye. The efficiencies of labeling in each of three enzymes were approximately 10 mol/mol of protein as dye content. FIG. 7 shows the histological pictures of biodistribution of three enzymes at the epiphyseal region at 6, 24, 72, and 168 h after a single intravenous infusion. FIG. 8 shows the average of the relative area of fluorescence. Three enzymes were distributed to the mineralized region, but not to the growth plate. At 6 h, the relative areas of fluorescence at the tagged enzymes were four-fold larger than the area at the untagged enzyme. Moreover, the fluorescence-labeled tagged enzymes retained until 168 h with two- to three-fold larger amount than the untagged enzyme. These results were consistent with the result of the in vitro hydroxyapatite affinity experiment. In liver, relatively high amount of enzyme distribution was observed compared to other tissues (data not shown). The distribution was widespread throughout the liver including hepatocytes and sinus-lining cells. The distribution patterns in liver were comparable among three enzymes. In other tissues including brain, lung, heart, spleen, and kidney, no significant difference was observed among three enzymes as well (data not shown).

Overall, the above results showed no biochemical and pharmacokinetic difference between two tagged enzymes.

Example 3

Figure 9:
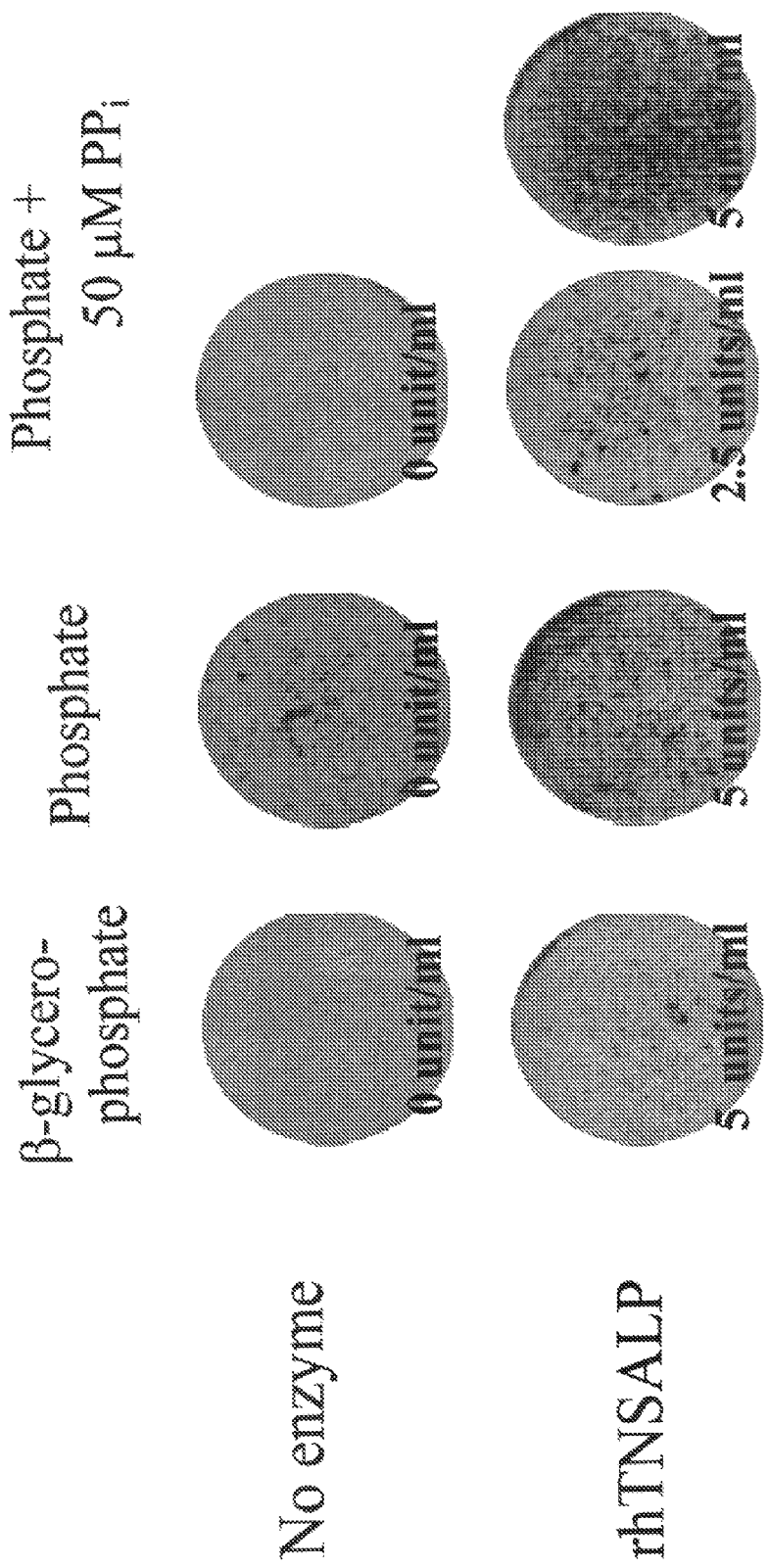
FIG. 9. In vitro mineralization experiment with anchorless rhTNSALP enzyme. The bone marrow cells derived from a hypophosphatasia patient were seeded in 12-well plate at a density of 10,000 cells/cm2, and differentiated under existing 2.5 mM Pi or 2.5 mM β-glycerophosphate as a phosphate source. The effect on mineralization of anchorless rhTNSALP enzyme was evaluated in the presence of PPi. The calcium deposits were visualized 12 days after the initiation of differentiation of bone marrow cells.

Effect of Anchorless rhTNSALP on Mineralization in the Presence of $PP_i$ in Primary Bone Marrow Cell Culture In human bone marrow cells derived from a hypophosphatasia patient, mineralization never occurred in the absence of TNSALP even when β-glycerophosphate was added. The addition of one of the enzyme resulted in marked recovery of mineralization (FIG. 9). In contrast, mineralization was observed when $P_i$ was used in the medium instead of β-glycerophosphate even in the absence of any enzyme. The presence of any of the enzymes did not provide any additive effect for the mineralization. These findings indicate that the anchorless rhTNSALP enzyme played a biological role in the mineralization process by providing free $P_i$ released during the hydrolysis of β-glycerophosphate. We added $PP_i$, an inhibitor of mineralization, to see whether the anchorless rhTNSALP enzyme hydrolyze $PP_i$ to restore the mineralization. $PP_i$ itself completely inhibited the mineralization even in the presence of $P_i$. The addition of the enzyme restored the mineralization level to $PP_i$-free control culture.

Example 4

Enzyme Replacement Therapy with Anchorless rhTNSALP

Figure 10:
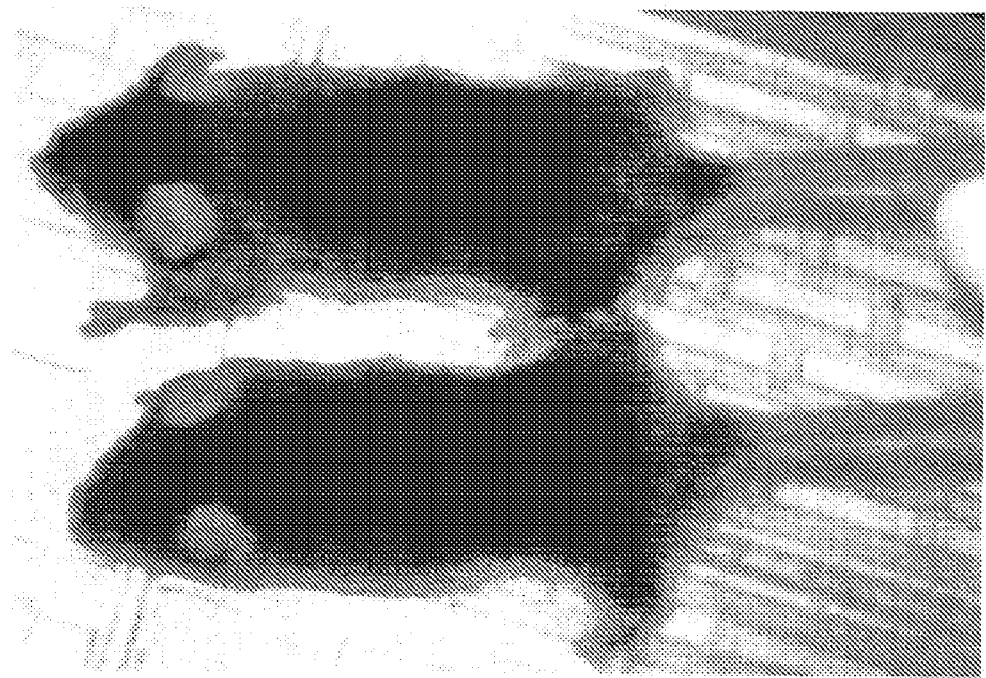
FIG. 10. Clinical phenotype of TNSALP (−/−) mouse treated by anchorless rhTNSALP. The upper mouse is a wild-type from the same littermate while the lower mouse is treated with anchorless rhTNSALP for 6 weeks. The stature and appearance of treated mouse is nearly the same as the wild-type control mouse.
Figure 11A:
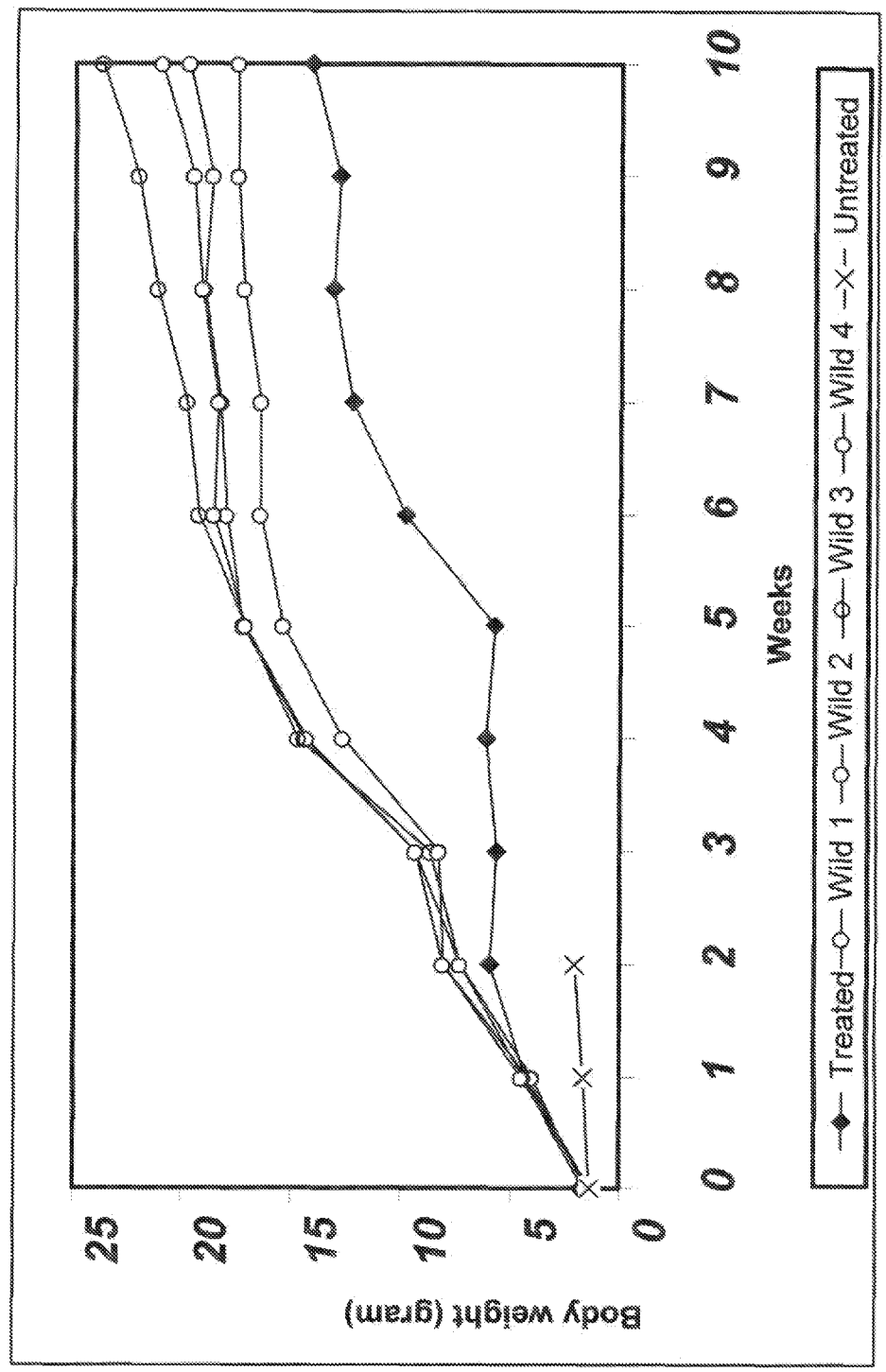
FIG. 11 Growth curve of mice injected with anchorless rhTNSALP of 5 mg/kg. A) Specimen 1, B) Specimen 2. TNSALP (−/−) mouse which received enzyme on the day after birth, followed by further weekly injection up to 10 weeks. At 0, 1, 2, 3, 4 weeks, the enzyme was injected by intraperitoneal. After 5 weeks through 10 weeks, enzyme was injected through tail vein weekly (black diamond line). The wild-type littermates of the treated TNSALP (−/−)(open circles). The untreated TNSALP (−/−). The untreated mice died before the weaning (x-x).
Figure 11B:
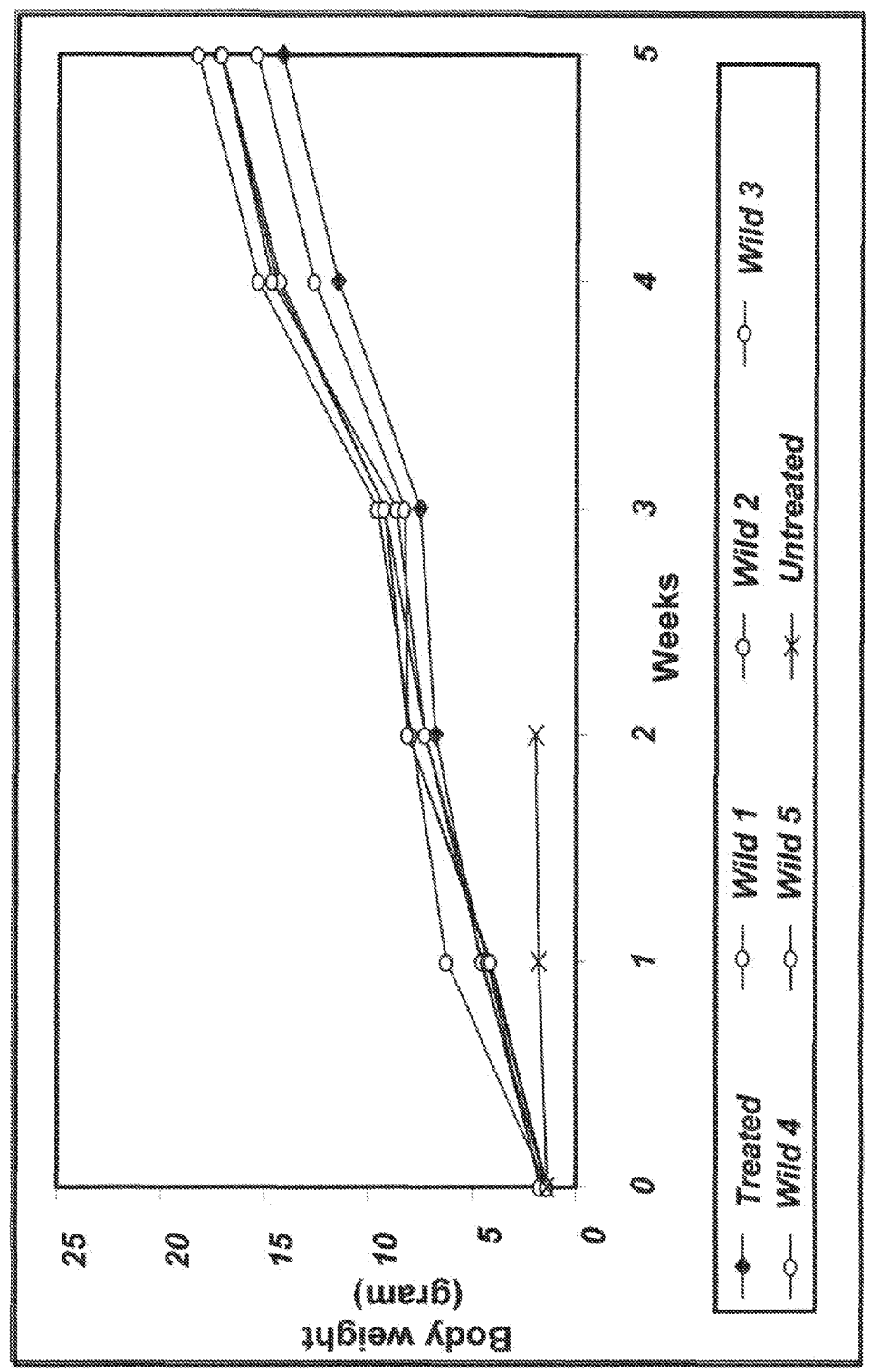

The TNSALP gene knock-out mouse strains as models for hypophosphatasia had <1% of wild-type plasma TNSALP activity. These TNSALP−/− mice were growth impaired, develop epileptic seizures and apnea, and died before weaning as described previously [39, 47, 48]. Postnatal growth of TNSALP−/− mice treated with anchorless rhTNSALP at 5 mg/kg of body weight and their littermate controls are shown in FIG. 10. The average life span of untreated TNSALP−/− mice without anchorless rhTNSALP enzyme administration was 10 days [39, 47, 48]. In treated mice, injected with anchorless rhTNSALP, no epileptic seizures appeared until at least 2 months old, in addition the mice lived approximately 4 and 7 times as long. Growth curves of TNSALP−/− mice and littermate controls without treatment are shown in FIG. 11 for comparison. One mouse treated with IP infusion for 4 weeks did not grow well (FIG. 11A). However after IV infusion began, the mouse increased its body weight substantially. A second mouse treated with IV infusion at birth grew well at subnormal levels (FIG. 11B). Both of these mice exhibited no abnormal activity and seizures.

Overall, ERT with the C-terminus anchorless rhTNSALP enzyme showed clinical effectiveness on TNSALP−/− mice.

Materials and Methods

Production of human recombinant acidic oligopeptide-tagged and untagged TNSALPs (GenBank: NM_000478.2)—The GPI anchoring signal peptide sequence of TNSALP (5'-CTTGCTGCAGGCCCCCTGCTGCTCGCTCTGGCCCTCTACCCCCTGAGCGTCCTGTTC-3': c.1516C to c.1572C: Leu506 to Phe524) (SEQ ID NO: 2) was deleted from the full-length of TNSALP cDNA to produce the enzymes as a secreted form. To produce acidic oligopeptide-tagged TNSALP, a stretch of six or eight of L-Asp (six L-Asp, 5'-GACGATGACGACGATGAT-3' (SEQ ID NO: 3): eight L-Asp, 5'-GATGATGATGATGATGATGACGAC-3'(SEQ ID NO: 4)) was introduced additionally at the C-terminus after c.1515C of Ser505 (CD6- or CD8-TNSALP, respectively) mediating a linker (5'-ACCGGTGAAGCAGAGGCC-3' (SEQ ID NO: 5)), followed by a termination codon. The three enzymes used for the further experiments were named as anchorless rhTNSALP (human TNSALP anchorless at the C-terminal), CD6-TNSALP (human TNSALP anchorless at the C-terminal tagged with a stretch of six L-Asp), and CD8-TNSALP (human TNSALP anchorless at the C-terminal tagged with a stretch of eight L-Asp), respectively.

For the preparation of the first strand cDNA, reverse transcriptase reaction was performed by using total RNA isolated from healthy human peripheral blood. To amplify rhTNSALP, CD6-TNSALP, and CD8-TNSALP cDNA, PCR reactions were carried out with the following primers: TNSALP, forward 5'-GAATTCACCCACGTCGATTGCATCTCTGGGCTCCAG-3' (SEQ ID NO: 6) and reverse 5'-ctcgagTCAGCTGCCTGCCGAGCTGGCAGGAGCAC-3'(SEQ ID NO: 7): CD6-TNSALP, forward 5'-GAATTCACCCACGTCGATTGCATCTCTGGGCTCCAG-3' (SEQ ID NO: 8) and reverse 5'-tcaatcatcgtcgtcatcgtcggcctctgcttcaccggtGCTGCCTGCCGAGCTG-GCAGGAGCACAGTG-3'(SEQ ID NO: 9): CD8-TNSALP, forward 5'-GAATTCACCCACGTCGATTGCATCTCTGGGCTCCAG-3' (SEQ ID NO: 10) and reverse 5'-tcagtcgtcatcatcatcatcatcgcctctgcttcaccggtGCTGCCTGCCGAGCTGGCAGGAGCAC AGTG-3'(SEQ ID NO: 11). The nucleotide sequences compatible with six or eight of L-Asp were added to the reverse primers used here. The amplified cDNA were cloned and sequenced. The cDNA were then transferred into EcoRI cloning sites of mammalian expression vector pCXN, kindly provided by Miyazaki J., Osaka University, Suita, Japan (40).

The anchorless rhTNSALP, CD6-TNSALP, and CD8-TNSALP cDNAs subcloned in pCXN were then transfected into Chinese hamster ovary (CHO-K1) cells with lipofectamine according to manufacture's instruction (Invitrogen). Selection of colonies was carried out in growth medium with Dulbecco's Modified Eagle Medium supplemented with 15% fetal bovine serum (FBS), plus 600 µg/ml G418 (Sigma-Aldrich) for 10-12 days. Individual clones were picked, grown to confluency, and analyzed for enzyme expression by measuring secreted enzyme activity in the medium as described below. The highest-producing clone was grown in collection medium with Ex-Cell™ 325 PF CHO Protein-free medium (JRH Biosciences) and 15% FBS. When the cells reached confluency, the cells were rinsed with PBS and fed with collection media without FBS to collect enzyme for purification.

Measurement of Alkaline Phosphatase Activity

A 50 μl of volume of sample was combined with 250 μl of 10 mM p-nitrophenyl phosphate (pNPP) (Sigma-Aldrich, MO) as a substrate in 1 M diethanolamine, pH 9.8, containing 1 mM magnesium chloride and 0.02 mM zinc chloride, and incubated at 37° C. The time-dependent increase in absorbance at 405 nm (reflecting p-nitrophenolate production) was measured on a plate spectrophotometer (EL800, Bio-Tek Instrument, Inc., VT). One unit of activity was defined as the quantity of enzyme that catalyzed the hydrolysis of 1 μmol substrate in 1 min.

Enzyme Purification

The anchorless rhTNSALP enzyme was purified by a two-step column procedure. Tris buffer was 25 mM Tris-HCl, pH 8.0, containing 0.1 mM magnesium chloride and 0.01 mM zinc chloride. Unless stated otherwise, all steps were performed at 4° C.

Step 1. The medium containing enzyme was filtered through a 0.2 μm filter, and then dialyzed against Tris buffer using Amicon stirred-cell ultrafiltration unit with Millipore ultrafiltration membrane YM-30.

Step 2. The dialyzed medium was applied to a column of DEAE Sepharose (Sigma-Aldrich, MO) equilibrated with Tris buffer. The column was first washed with Tris buffer, and then the enzyme was eluted with 0-0.4 M NaCl in a linear gradient.

Step 3. The active eluted fractions were pooled and dialyzed against Tris buffer containing 0.1 M NaCl by using Centricon centrifugal filter device with Millipore ultrafiltration YM-10 filter. The dialyzed fractions were then concentrated for step 4.

Step 4. The concentrated enzyme was applied to a column of Sephacryl S-400-HR (Sigma-Aldrich, MO) equilibrated with Tris buffer containing 0.1 M NaCl. The enzyme was eluted with Tris buffer containing 0.1 M NaCl.

Step 5. The active eluted fractions were pooled and dialyzed against Tris buffer containing 0.1 M NaCl by using Centricon centrifugal filter device with Millipore ultrafiltration YM-10 filter. The dialyzed fractions were then concentrated and stored at −80° C. until use.

Polyacrylamide Gel Electrophoresis

Polyacrylamide gel electrophoresis in the presence of sodium dodecyl sulfate (SDS-PAGE) was performed, followed by silver staining [44, 45].

Hydroxyapatite binding assay—Hydroxyapatite beads (Sigma-Aldrich) were suspended in 25 mM Tris-HCl buffered saline (TBS), pH 7.4, at concentration of 100 μg/100 μl. The purified enzyme was mixed with the hydroxyapatite suspension at a final concentration of 1.0, 2.5, 5.0, and 10.0 μg/ml. The mixture was mixed at 37° C. for 1 h, and centrifuged at 14,000×rpm for 10 min to separate unbound enzyme and bound enzyme. To determine unbound enzyme, enzyme activity in supernatant was measured, and bound enzyme was determined from the amount of total enzyme and unbound enzyme. Binding constant ($K_b$) and maximal binding rate ($B_{max}$) were determined from double-reciprocal plots.

Lectin Affinity Chromatography

To evaluate the carbohydrate chain structure of the enzymes, we applied the enzymes to lectin affinity chromatography. TBS used here was 10 mM Tris-HCl, pH 8.0, supplemented with 0.5 M sodium chloride, 1 mM calcium chloride, 1 mM magnesium chloride, 1 mM manganese chloride and 0.01 mM zinc chloride. The column of the concanavalin A (*Canavalia ensiformis*, ConA)-sepharose 4B (Sigma-Aldrich) and the wheat germ agglutinin (*Triticum vulgaris*, WGA)-agarose CL-4B (Fluka) were equilibrated with TBS at a flow rate of 0.2 ml/min. Lectin affinity chromatography was performed as described previously [43]. Briefly, the purified enzyme in 0.6 ml of TBS was applied to the ConA and WGA columns, and left to stand for 3 h at room temperature. Three fractions were obtained by using two different concentrations, 0.01 M and 0.5 M of α-methyl-D-mannopyranoside (αMM) (Sigma-Aldrich) from ConA column, and 0.1 M and 0.5 M of N-acetyl-D-glucosamine (GlcNAc) (Sigma-Aldrich) from the WGA column: unbound fraction, weakly-bound fraction, and strongly-bound fraction.

Neuraminidase Digestion

Tagged and non-tagged rhTNSALPs were digested with α(2 3, 6, 8, 9) neuraminidase (*Arthrobacter ureafaciens*) (Sigma-Aldrich) to clarify the content of sialic acids at the carbohydrate chain. Twenty units of each purified TNSALP enzyme were exposed to 0.01 unit of neuraminidase in 250 mM sodium phosphate, pH 6.0, overnight at room temperature. The digested enzyme was then analyzed for polyacrylamide gel electrophoresis and lectin affinity chromatography, as described above.

Biodistribution of Alexa-Labeled Enzymes

One mg/ml of purified enzymes were labeled with Alexa Fluor 546 Protein Labeling Kit following manufacture's instruction (Molecular Probes). The Alexa-labeled enzyme was injected to B6 mice (6-7 weeks old) from tail vein at a dose of 1 mg/kg of body weight. Mice were sacrificed at 6, 24, 72, and 168 h after a single infusion, and multiple tissues including brain, lung, heart, liver, spleen, kidney, and leg were dissected. The tissues were immersion-fixed in 10% neutral buffered formalin, embedded in paraffin, and sectioned. Tissues were studied by fluorescence microscopy for evaluation of enzyme distribution, and the areas of fluorescence from three fields of fluorescent images around growth plate were quantitated by using AlphaEaseFC (Alpha Innotech Corp.).

In Vitro Mineralization Assay

To evaluate the level of bioactivity of the anchorless rhTNSALP enzyme, in vitro mineralization experiments were performed using bone marrow cells derived from a hypophosphatasia patient with an infantile form (10 month old). The bone marrow cells were seeded into 150×25 mm tissue culture dishes. These cells were allowed to attach without disturbance for seven days in growth medium consisting of minimum essential medium alpha (MEMα) supplemented with 10% FBS, 50 units/ml penicillin, and 50 μg/ml streptomycin sulfate. The medium was then replaced to fresh growth medium at 3-day intervals. When the cells reached confluency, they were subcultured in the 12-well plates at a density of 10,000 cells/cm². On the following day, the growth medium was replaced with the differentiation medium: with MEMα supplemented with 10% FBS, 50 units/ml penicillin, 50 μg/ml streptomycin sulfate, 0.3 mM ascorbic acid, and 100 nM dexamethasone. The differentiation medium also included 2.5 mM $P_i$ or β-glycerophosphate as a phosphate source as well as either anchorless rhTNSALP at 2.5 or 5.0 units/ml. To further investigate the effect of the three enzymes on mineralization in the presence of $PP_i$, 50 μM $PP_i$ was added always with each enzyme to the bone marrow cell culture throughout the differentiation period. The differentiation medium was replaced at 3-day intervals. At 12 days after the initiation of the differentiation of the cells, the cells were fixed with 4% paraformaldehyde, followed by staining with Alizarin Red S to detect calcium phosphate deposits [46].

Long Term ERT with Anchorless rhTNSALP to Evaluate Clinical Effectiveness.

Long term ERT was performed using the anchorless rhTNSALP enzyme described above. The cephalic vein is the preferred injection rout at birth but is not visible after about 1 week. Intraperitoneal injections were administered from 1 to 4 weeks until the tail vain became visible. Three littermates remained untreated. Two mice (Specimens 1 and 2) received treatments of 5 mg/kg of body weight. Specimen received enzyme by cephalic vein injection on the day following birth, followed by weekly intraperitoneal injections at 0, 1, 2, 3, and 4 weeks and tail vein injections from 5 through 10 weeks. Similarly a Specimen 2 received enzyme on the day following birth by cephalic vein injection, followed by weekly intraperitoneal injections at 1, 2, and 3, weeks after which injection was administered though the tail vein From 4 through 10 weeks.

REFERENCES

The following numbered references are cited throughout this disclosure. These references are herein incorporated by reference. Applicants reserve the right to challenge the veracity of any statement made in these references.

[1] D. Fraser, Hypophosphatasia. Am. J. Med. 22 (1957) 730-746.
[2] M. P. Whyte, Hypophosphatasia, in: C. R. Scriver, A. L. Beaudet, W. S. Sly, D. Valle (Eds), The Metabolic and Molecular Bases of Inherited Disease, eighth ed., McGraw-Hill, New York, 2001, pp. 5313-5329.
[3] M. M. Silver, G. A. Vilos, K. J. Milne, Pulmonary hypophosphatasia in neonatal hypophosphatasia. Pediatr. Pathol. 8 (1988) 483-493.
[4] S. Y. Ali, Matrix formation and mineralization in bone, in: C. C. Whitehead (Ed), Bone biology and skeletal disorders, Carfax Publishing Co., Abingdon, U.K., 1992, pp. 19-38.
[5] H. C. Anderson, Molecular biology of matrix vesicles. Clin. Orthop. Relat. Res. 314 (1995) 266-280.
[6] A. L. Boskey, B. D. Boyan, Z. Schwartz, Matrix vesicles promote mineralization in a gelatin gel. Calcif. Tissue Int. 60 (1997) 309-315.
[7] A. L. Boskey, Amorphous calcium phosphate: the contention of bone. J. Dent. Res. 76 (1997) 1433-1436.
[8] H. C. Anderson, Mechanisms of pathologic calcification. Rheum. Dis. Clin. North Am. 14 (1988) 303-319.
[9] L. F. Bonewald, Z. Schwartz, L. D. Swain, B. D. Boyan, Stimulation of matrix vesicle enzyme activity in osteoblast-like cells by 1,25(OH)2D3 and transforming growth factor beta (TGF beta). Bone Miner. 17 (1992) 139-144.
[10] K. N. Fedde, Human osteosarcoma cells spontaneously release matrix-vesicle-like structures with the capacity to mineralize. Bone Miner. 17 (1992) 145-151.
[11] H. Fleisch, R. G. Russell, F. Straumann, Effect of pyrophosphate on hydroxyapatite and its implications in calcium homeostasis. Nature 212 (1966) 901-903.
[12] A. S. de Jong, T. J. Hak, P. van Duijn, The dynamics of calcium phosphate precipitation studied with a new polyacrylamide steady state matrix-model: influence of pyrophosphate collagen and chondroitin sulfate. Connect. Tissue Res. 7 (1980) 73-79.
[13] J. L. Meyer, Can biological calcification occur in the presence of pyrophosphate? Arch. Biochem. Biophys. 15 (1984) 1-8.
[14] D. W. Moss, R. H. Eaton, J. K. Smith, L. G. Whitby, Association of inorganic-pyrophosphatase activity with human alkaline-phosphatase preparations. Biochem. J. 102 (1967) 53-57.
[15] F. A. Leon, L. A. Rezende, P. Ciancaglini, J. M. Pizauro, Allosteric modulation of pyrophosphatase activity of rat osseous plate alkaline phosphatase by magnesium ions. Int. J. Biochem. Cell Biol. 30 (1998) 89-97.
[16] R. G. Russell, S. Bisaz, A. Donath, D. B. Morgan, H. Fleisch, Inorganic pyrophosphate in plasma in normal persons and in patients with hypophosphatasia, osteogenesis imperfecta, and other disorders of bone. J. Clin. Invest. 50 (1971) 961-965.
[17] E. Sorensen, H. Flodgaard, Adult hypophosphatasia. Acta. Med. Scand. 197 (1975) 357-360.
[18] S. A. Sorensen, H. Flodgaard, E. Sorensen, Serum alkaline phosphatase, serum pyrophosphatase, phosphorylethanolamine and inorganic pyrophosphate in plasma and urine. A genetic and clinical study of hypophosphatasia. Monogr. Hum. Genet. 10 (1978) 66-69.
[19] H. C. Anderson, Pyrophosphate stimulation of calcium uptake into cultured embryonic bones. Fine structure of matrix vesicles and their role in calcification. Dev. Biol. 34 (1973) 211-227.
[20] H. C. Anderson, H. H. Hsu, D. C. Morris, K. N. Fedde, M. P. Whyte, Matrix vesicles in osteomalacic hypophosphatasia bone contain apatite-like mineral crystals. Am. J. Pathol. 151 (1997) 1555-1561.
[21] H. C. Anderson, J. B. Sipe, L. Hessle, R. Dhanyamraju, E. Atti, N. P. Camacho, J. L. Millan, Impaired calcification around matrix vesicles of growth plate and bone in alkaline phosphatase-deficient mice. Am. J. Pathol. 164 (2004) 841-847.
[22] N. W. Barton, R. O. Brady, J. M. Dambrosia, A. M. Di Bisceglie, S. H. Doppelt, S. C. Hill, H. J. Mankin, G. J. Murray, R. I. Parker, C. E. Argoff, et al Replacement therapy for inherited enzyme deficiency-macrophage-targeted glucocerebrosidase for Gaucher's disease. N. Engl. J. Med. 324 (1991) 1464-1470.
[23] M. S. Sands, C. Vogler, J. W. Kyle, J. H. Grubb, B. Levy, N. Galvin, W. S. Sly, E. H. Birkenmeier, Enzyme replacement therapy for murine mucopolysaccharidosis type VII. J. Clin. Invest. 93 (1994) 2324-2331.
[24] R. M. Shull, E. D. Kakkis, M. F. McEntee, S. A. Kania, A. J. Jonas, E. F. Neufeld, Enzyme replacement in a canine model of Hurler syndrome. Proc. Natl. Acad. Sci. 91 (1994) 12937-12941.
[25] A. C. Crawley, D. A. Brooks, V. J. Muller, B. A. Petersen, E. L. Isaac, J. Bielicki, B. M. King, C. D. Boulter, A. J. Moore, N. L. Fazzalari, D. S. Anson, S. Byers, J. J. Hopwood, Enzyme replacement therapy in a feline model of Maroteaux-Lamy syndrome. J. Clin. Invest. 97 (1996) 1864-1873.
[26] E. D. Kakkis, J. Muenzer, G. E. Tiller, L. Waber, J. Belmont, M. Passage, B. Izykowski, J. Phillips, R. Doroshow, I. Walot, R. Hoft, E. F. Neufeld, Enzyme-replacement therapy in mucopolysaccharidosis I. N. Engl. J. Med. 344 (2001) 182-188.
[27] G. Altarescu, S. Hill, E. Wiggs, N. Jeffries, C. Kreps, C. C. Parker, R. O. Brady, N. W. Barton, R. Schiffmann, The efficacy of enzyme replacement therapy in patients with chronic neuronopathic Gaucher's disease. J. Pediatr. 138 (2001) 539-547.
[28] C. M. Eng, N. Guffon, W. R. Wilcox, D. P. Germain, P. Lee, S. Waldek, L. Caplan, G. E. Linthorst, R. J. Desnick, International Collaborative Fabry Disease Study Group, Safety and efficacy of recombinant human alpha-galactosidase A-replacement therapy in Fabry's disease. N. Engl. J. Med. 345 (2001) 9-16.

[29] F. S. Furbish, C. J. Steer, N. L. Krett, J. A. Barranger, Uptake and distribution of placental glucocerebrosidase in rat hepatic cells and effects of sequential deglycosylation. Biochim. Biophys. Acta. 673 (1981) 425-434.

[30] G. J. Murray, Lectin-specific targeting of lysosomal enzymes to reticuloendothelial cells. Methods Enzymol. 149 (1987) 25-42.

[31] P. D. Stahl, J. S. Rodman, M. J. Miller, P. H. Schlesinger, Evidence for receptor-mediated binding of glycoproteins, glycoconjugates, and glycosidases by alveolar macrophages. Proc. Natl. Acad. Sci. 75 (1978) 1399-1403.

[32] D. T. Achord, F. E. Brot, C. E. Bell, W. S. Sly, Human beta-glucuronidase: in vivo clearance and in vitro uptake by a glycoprotein recognition system on reticuloendothelial cells. Cell 15 (1978) 269-278.

[33] J. A. Barranger, E. O'Rourke, Lessons learned from the development of enzyme therapy for Gaucher disease. J. Inherit. Metab. Dis. 24 (2001) 89-96.

[34] M. P. Whyte, R. Valdes, L. M. Ryan, W. H. McAlister, Infantile hypophosphatasia: enzyme replacement therapy by intravenous infusion of alkaline phosphatase-rich plasma from patients with Paget bone disease. J. Pediatr. 101 (1982) 379-386.

[35] M. P. Whyte, W. H. McAlister, L. S. Patton, H. L. Magill, M. D. Fallon, W. B. Lorentz, H. G. Herrod, Enzyme replacement therapy for infantile hypophosphatasia attempted by intravenous infusions of alkaline phosphatase-rich Paget plasma: results in three additional patients. J. Pediatr. 105 (1984) 926-933.

[36] M. P. Whyte, H. L. Magill, M. D. Fallon, H. G. Herrod, Infantile hypophosphatasia: normalization of circulating bone alkaline phosphatase activity followed by skeletal remineralization. Evidence for an intact structural gene for tissue nonspecific alkaline phosphatase. J. Pediatr. 108 (1986) 82-88.

[37] M. Weninger, R. A. Stinson, H. Plenk, P. Böck, A. Pollak, Biochemical and morphological effects of human hepatic alkaline phosphatase in a neonate with hypophosphatasia. Acta Paediatr. Scand. Suppl. 360 (1989) 154-160.

[38] M. P. Whyte, M. Landt, L. M. Ryan, R. A. Mulivor, P. S. Henthorn, K. N. Fedde, J. D. Mahuren, S. P. Coburn, Alkaline phosphatase: placental and tissue-nonspecific isoenzymes hydrolyze phosphoethanolamine, inorganic pyrophosphatem and pyridoxal 5'-phosphate. Substrate accumulation in carriers of hypophosphatasia corrects during pregnancy. J. Clin. Invest. 95 (1995) 1440-1445.

[39] S, Narisawa, C. Wennberg, J. L. Millan. Abnormal vitamin B6 metabolism in alkaline phosphatase knock-out mice causes multiple abnormalities, but not the impaired bone mineralization. J. Pathol. 191 (2001) 125-133.

[40] T. Nishioka, S. Tomatsu, M. A. Gutierrez, K. I. Miyamoto, G. G. Trandafirescu, P L Lopez, G. H. Grubb, R. Kanai, H. Kobayashi, S. Yamaguchi, G. S. Gottesman, R. Cahill, A. Noguchi, K. Miyamoto, W. S. Sly. Enhancement of drug delivery to bone: Characterization of human tissue-nonspecific alkaline phosphatase tagged with an acidic oligopeptide. Mol Genet Metab. 2006 July; 88(3):244-255. Epub 2006 Apr. 17.

[41] Kasugai, S., Fujisawa, R., Waki, Y., Miyamoto, K., and Ohya, K. (2000) J. Bone. Miner. Res. 15, 936-943

[42] Yokogawa, K., Miya, K., Sekido, T., Higashi, Y., Nomura, M., Fujisawa, R., Morito, K., Masamune, Y., Waki, Y., Kasugai, S., and Miyamoto, K. (2001) Endocrinology 142, 1228-1233

[43] Koyama, I., Sakagishi, Y., and Komoda, T. (1986) J. Chromatogr. 374 51-59

[44] U. K. Laemmli, Cleavage of structural proteins during the assembly of the head of bacteriophage T4. Nature 227 (1970) 680-685.

[45] C. R. Merril, D. Goldman, M. L. Van Keuren, Silver staining methods for polyacrylamide gel electrophoresis. Methods Enzymol. 96 (1983) 230-239.

[46] S. M. McGEE-RUSSELL, Histochemical methods for calcium. J. Histochem. Cytochem. 6 (1958) 22-42.

[47] K. G. Waymire, J. D. Mahuren, J. M. Jaje, T. R. Guilarte, S. P. Coburn, G. R. MacGregor, Mice lacking tissue nonspecific alkaline phosphatase die from seizures due to defective metabolism of vitamin B-6. Nat. Genet. 11 (1995) 45-51.

[48] S, Narisawa, N. Frohlander, J. L. Millan, Inactivation of two mouse alkaline phosphatase genes and establishment of a model of infantile hypophosphatasia. Dev. Dyn. 208 (1997) 432-446.

---

We claim:

1. A method for increasing life span or increasing bone mineralization or increasing body weight or reducing epileptic seizure in an animal having hypophosphatasia by injecting the animal with an effective amount of a composition comprising a physiologically active, untagged secreted soluble anchorless recombinant human tissue non-specific alkaline phosphatase (rhTNSALP) substantially purified from the culture media of a cultured cell expressing a nucleic acid molecule encoding a rhTNSALP having the glycosylphosphatidylinositol anchoring signal peptide deleted, whereby life span or bone mineralization or body weight is increased in the animal or epileptic seizure is decreased in the animal.

2. The method of claim 1, wherein the amino acid sequence of the rhTNSALP consists of the sequence set forth in amino acid residues 1-505 of SEQ ID NO:1.

3. The method of claim 1, wherein the specific activity of the substantially purified rhTNSALP is about 2744 units per milligram of protein.

4. The method of claim 1, wherein the composition further comprises an injectable aqueous solution.

5. The method of claim 1, wherein the amount of rhTNSALP is a weekly dosage.

6. The method of claim 1, wherein the amount of rhTNSALP is equal to about 5 milligrams per kilogram of the animal to be treated.

7. The method of claim 1, wherein the amount of rhTNSALP is equal to about 10 units per gram of the animal to be treated.

8. The method of claim 1, wherein said animal is a human.

9. A method for increasing life span or increasing bone mineralization or increasing body weight or reducing epileptic seizure in an animal having hypophosphatasia comprising injecting the animal with an effective amount of a composition, the composition including:

a) an injectable aqueous solution, and b) a physiologically active, untagged secreted soluble anchorless recombinant human tissue nonspecific alkaline phosphatase (rhTNSALP) substantially purified from the culture media of a cultured cell expressing a nucleic acid molecule encoding a rhTNSALP having the glycosylphosphatidylinositol anchoring signal peptide deleted, whereby life span or bone mineralization or body weight is increased in the animal or epileptic seizure is decreased in the animal.

10. The method of claim 9, wherein the amino acid sequence of the rhTNSALP consists of the sequence set forth in amino acid residues 1-505 of SEQ ID NO:1.

11. The method of claim 9, wherein the amount of rhTNSALP administered is used to treat the animal for one week.

12. The method of claim 11, wherein a weekly dosage comprises about 10 units of the rhTNSALP per gram of the animal being treated.

13. The method of claim 11, wherein a weekly dosage comprises about 5 milligrams of the rhTNSALP per kilogram of the animal to be treated.

14. The method of claim 9, wherein the specific activity of the substantially purified rhTNSALP is about 2744 units per milligram of protein.

15. The method of claim 9, wherein said animal is a human.

16. A method for increasing life span or increasing bone mineralization or increasing body weight or reducing epileptic seizure in an animal having hypophosphatasia comprising injecting the animal with an effective amount of a composition, the composition including:

a) an injectable aqueous solution, and b) a physiologically active, untapped secreted soluble anchorless recombinant human tissue nonspecific alkaline phosphatase (rhTNSALP) substantially purified from the culture media of a cultured cell expressing a nucleic acid molecule encoding a rhTNSALP having the glycosylphosphatidylinositol anchoring signal peptide deleted, wherein, i. the specific activity of the substantially purified rhTNSALP is about 2744 units per milligram of protein, and ii. the amount of rhTNSALP administered is equal to a weekly dosage of about 10 units per gram of the animal to be treated.

17. The method of claim 16, wherein the amino acid sequence of the rhTNSALP consists of the sequence set forth in amino acid residues 1-505 of SEQ ID NO:1.

18. The method of claim 16, wherein said animal is a human.

* * * * *

UNITED STATES PATENT AND TRADEMARK OFFICE
CERTIFICATE OF CORRECTION

PATENT NO. : 7,943,126 B2
APPLICATION NO. : 12/405920
DATED : May 17, 2011
INVENTOR(S) : Shunji Tomatsu et al.

It is certified that error appears in the above-identified patent and that said Letters Patent is hereby corrected as shown below:

Title Page, Item (56) OTHER PUBLICATIONS, in Eng et al., replace "N. Eng!. J. Med." with --N. Engl. J. Med.--;

Title Page, Item (56) in Whyte et al., Enzyme replacement..., replace "infusions of \ / alkaline" with --infusions of alkaline--;

Title Page, Item (56) in Weninger et al., replace "SUppl." with --Suppl.--.

Title Page 2, Item (56) under OTHER PUBLICATIONS, in Narlsawa et al., Abnormal vitamin..., replace "mUltiple" with --multiple--;

In M. Whyte, Hypophosphatasia..., replace "vol. 15," with --Vol. 15,0--;

In Weiss et al., replace "Liver/Bone1Kidney" with --Liver/Bone/Kidney--;

In Weiss et al., replace "Phasphatase" with --Phosphatase--.

Column 1, Line 35, replace "ALP know as" with --ALP known as--.

Column 8, Line 15, replace "referees" with --refers--;

Line 57, replace "is know to facilitate" with --are known to facilitate--;

Line 58, replace "be know to possess" with --be known to possess--.

Column 13, Line 45, replace "PP$_i$an inhibitor" with --PP$_i$, an inhibitor--.

Column 14, Line 63, replace "manufacture's instruction" with --manufacturer's instruction--.

Signed and Sealed this
Twelfth Day of February, 2013

Teresa Stanek Rea
*Acting Director of the United States Patent and Trademark Office*

CERTIFICATE OF CORRECTION (continued)
U.S. Pat. No. 7,943,126 B2

Column 16, Line 31, replace "manufacture's instruction" with --manufacturer's instruction--.

Column 17, Line 8, replace "rout" with --route--;

Line 16, replace "Similarly a Specimen 2 received" with --Similarly Specimen 2 received--;

Line 19, replace "though" with --through--.

Column 20, Line 8, in [39], replace "S, Narisawa" with --S. Narisawa--;

Line 40, in [48], replace "S, Narisawa" with --S. Narisawa--.

SEQUENCE LISTING

```
<160> NUMBER OF SEQ ID NOS: 1

<210> SEQ ID NO 1
<211> LENGTH: 524
<212> TYPE: PRT
<213> ORGANISM: Homo sapiens
<220> FEATURE:
<221> NAME/KEY: GPI ANCHOR SIGNAL
<222> LOCATION: (506)..(524)

<400> SEQUENCE: 1

Met Ile Ser Pro Phe Leu Val Leu Ala Ile Gly Thr Cys Leu Thr Asn
1               5                   10                  15

Ser Leu Val Pro Glu Lys Glu Lys Asp Pro Lys Tyr Trp Arg Asp Gln
            20                  25                  30

Ala Gln Glu Thr Leu Lys Tyr Ala Leu Glu Leu Gln Lys Leu Asn Thr
        35                  40                  45

Asn Val Ala Lys Asn Val Ile Met Phe Leu Gly Asp Gly Met Gly Val
```

-continued

```
            50                  55                  60
Ser Thr Val Thr Ala Ala Arg Ile Leu Lys Gly Gln Leu His His Asn
65                  70                  75                  80

Pro Gly Glu Glu Thr Arg Leu Glu Met Asp Lys Phe Pro Phe Val Ala
                85                  90                  95

Leu Ser Lys Thr Tyr Asn Thr Asn Ala Gln Val Pro Asp Ser Ala Gly
                100                 105                 110

Thr Ala Thr Ala Tyr Leu Cys Gly Val Lys Ala Asn Glu Gly Thr Val
                115                 120                 125

Gly Val Ser Ala Ala Thr Glu Arg Ser Arg Cys Asn Thr Thr Gln Gly
130                 135                 140

Asn Glu Val Thr Ser Ile Leu Arg Trp Ala Lys Asp Ala Gly Lys Ser
145                 150                 155                 160

Val Gly Ile Val Thr Thr Arg Val Asn His Ala Thr Pro Ser Ala
                165                 170                 175

Ala Tyr Ala His Ser Ala Asp Arg Asp Trp Tyr Ser Asp Asn Glu Met
                180                 185                 190

Pro Pro Glu Ala Leu Ser Gln Gly Cys Lys Asp Ile Ala Tyr Gln Leu
                195                 200                 205

Met His Asn Ile Arg Asp Ile Asp Val Ile Met Gly Gly Gly Arg Lys
                210                 215                 220

Tyr Met Tyr Pro Lys Asn Lys Thr Asp Val Glu Tyr Glu Ser Asp Glu
225                 230                 235                 240

Lys Ala Arg Gly Thr Arg Leu Asp Gly Leu Asp Leu Val Asp Thr Trp
                245                 250                 255

Lys Ser Phe Lys Pro Arg Tyr Lys His Ser His Phe Ile Trp Asn Arg
                260                 265                 270

Thr Glu Leu Leu Thr Leu Asp Pro His Asn Val Asp Tyr Leu Leu Gly
                275                 280                 285

Leu Phe Glu Pro Gly Asp Met Gln Tyr Glu Leu Asn Arg Asn Asn Val
                290                 295                 300

Thr Asp Pro Ser Leu Ser Glu Met Val Val Ala Ile Gln Ile Leu
305                 310                 315                 320

Arg Lys Asn Pro Lys Gly Phe Phe Leu Leu Val Glu Gly Gly Arg Ile
                325                 330                 335

Asp His Gly His His Glu Gly Lys Ala Lys Gln Ala Leu His Glu Ala
                340                 345                 350

Val Glu Met Asp Arg Ala Ile Gly Gln Ala Gly Ser Leu Thr Ser Ser
                355                 360                 365

Glu Asp Thr Leu Thr Val Val Thr Ala Asp His Ser His Val Phe Thr
370                 375                 380

Phe Gly Gly Tyr Thr Pro Arg Gly Asn Ser Ile Phe Gly Leu Ala Pro
385                 390                 395                 400

Met Leu Ser Asp Thr Asp Lys Lys Pro Phe Thr Ala Ile Leu Tyr Gly
                405                 410                 415

Asn Gly Pro Gly Tyr Lys Val Val Gly Gly Glu Arg Glu Asn Val Ser
                420                 425                 430

Met Val Asp Tyr Ala His Asn Asn Tyr Gln Ala Gln Ser Pro Val Pro
                435                 440                 445

Leu Arg His Glu Thr His Gly Gly Glu Asp Val Ala Val Phe Ser Lys
                450                 455                 460

Gly Pro Met Ala His Leu Leu His Gly Val His Glu Gln Asn Tyr Val
465                 470                 475                 480
```

```
-continued

Pro His Val Met Ala Tyr Ala Ala Cys Ile Gly Ala Asn Leu Gly His
            485                 490                 495

Cys Ala Pro Ala Ser Ser Ala Gly Ser Leu Ala Ala Gly Pro Leu Leu
            500                 505                 510

Leu Ala Leu Ala Leu Tyr Pro Leu Ser Val Leu Phe
            515             520
```